(12) United States Patent
Hart

(10) Patent No.: US 8,754,012 B2
(45) Date of Patent: Jun. 17, 2014

(54) METHOD FOR DETERMINING PROTEIN SOLUBILITY

(75) Inventor: Darren James Hart, Grenoble (FR)

(73) Assignee: European Molecular Biology Laboratory, Heidelberg (DE)

( * ) Notice: Subject to any disclaimer, the term of this patent is extended or adjusted under 35 U.S.C. 154(b) by 1381 days.

(21) Appl. No.: 11/661,762

(22) PCT Filed: Sep. 5, 2005

(86) PCT No.: PCT/GB2005/003417
§ 371 (c)(1),
(2), (4) Date: Apr. 11, 2007

(87) PCT Pub. No.: WO2006/024875
PCT Pub. Date: Mar. 9, 2006

(65) Prior Publication Data
US 2008/0132425 A1    Jun. 5, 2008

(30) Foreign Application Priority Data
Sep. 3, 2004   (GB) .................................. 0419628.3

(51) Int. Cl.
C40B 20/04    (2006.01)
C40B 20/08    (2006.01)
C40B 30/04    (2006.01)

(52) U.S. Cl.
USPC ...................................... 506/4; 506/6; 506/9

(58) Field of Classification Search
USPC .................................................... 506/4, 6, 9
See application file for complete search history.

(56) References Cited

U.S. PATENT DOCUMENTS

| 5,723,584 | A | * | 3/1998 | Schatz ......................... 530/408 |
| 5,834,593 | A | * | 11/1998 | Prusiner et al. ................ 530/350 |
| 6,077,689 | A | * | 6/2000 | Snavely ....................... 435/69.1 |
| 7,223,742 | B2 | * | 5/2007 | Snavely ....................... 514/44 R |
| 7,718,381 | B2 | * | 5/2010 | Nordlund et al. .............. 435/7.2 |
| 7,790,420 | B2 | * | 9/2010 | Hart et al. ................... 435/91.42 |
| 2003/0119094 | A1 | * | 6/2003 | Lesley et al. ................. 435/69.1 |
| 2004/0170976 | A1 | * | 9/2004 | Lesley et al. ...................... 435/6 |
| 2005/0221308 | A1 | * | 10/2005 | Samaddar et al. ................ 435/6 |

FOREIGN PATENT DOCUMENTS

| EP | 1 295 894 | * | 3/2003 | ............... C07K 1/13 |
| WO | WO 03/064656 | * | 8/2003 | ............. C12N 15/62 |

OTHER PUBLICATIONS

Kapust et al., 1999, Escherichia coli maltose-binding protein is uncommonly effective at promoting the solubility of polypeptides to which it is fused, Protein Science, 8: 1668-1674.*
Makrides, 1996, Strategies for Achieving High-Level Expression fo Genes in Escherichia coli, Microbiological Reviews, 60(3): 512-538.*
Waldo, 2003, Genetic screens and directed evolution for protein solubility, Current Opinion in Chemical Biology, 7: 33-38.*
D. Beckett et al., "A Minimal Peptide Substrate in Biotin Holoenzyme Synthetase-Catalyzed Biotinylation", Protein Science, vol. 8, pp. 921-929, 1999.

* cited by examiner

*Primary Examiner* — Amber D Steele
(74) *Attorney, Agent, or Firm* — Wenderoth, Lind & Ponack, L.L.P.

(57) ABSTRACT

The present invention relates to methods of screening for expression of a soluble candidate protein within an expression library of candidate proteins. The method involves fusing each candidate protein in the library to a peptide substrate and identifying cells that express soluble candidate protein by detecting enzymatic modification of the peptide substrate.

19 Claims, 22 Drawing Sheets

FIGURE 5
5a
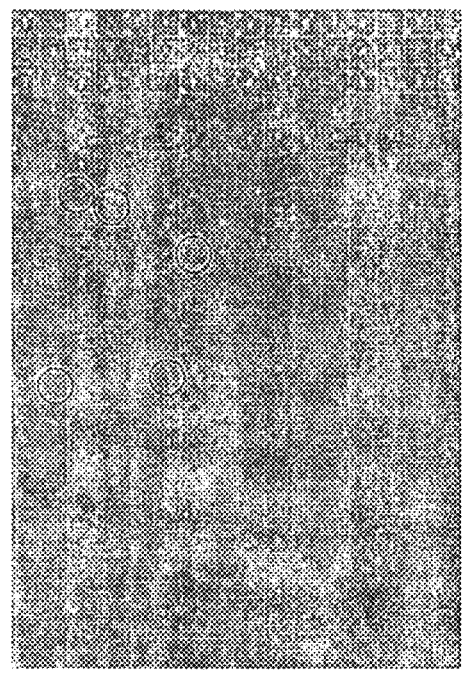
5b
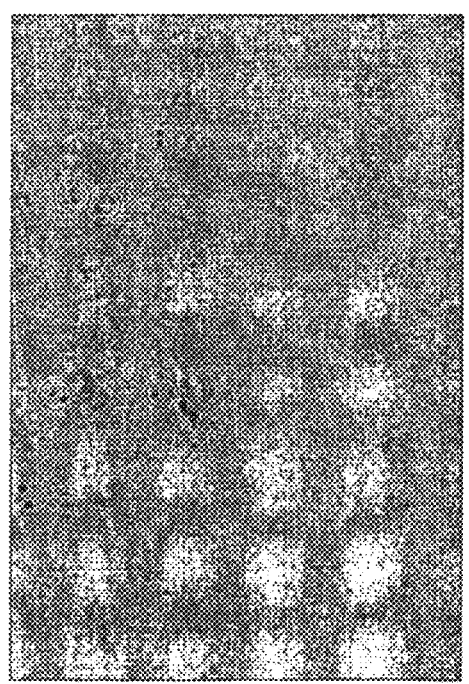

FIGURE 12
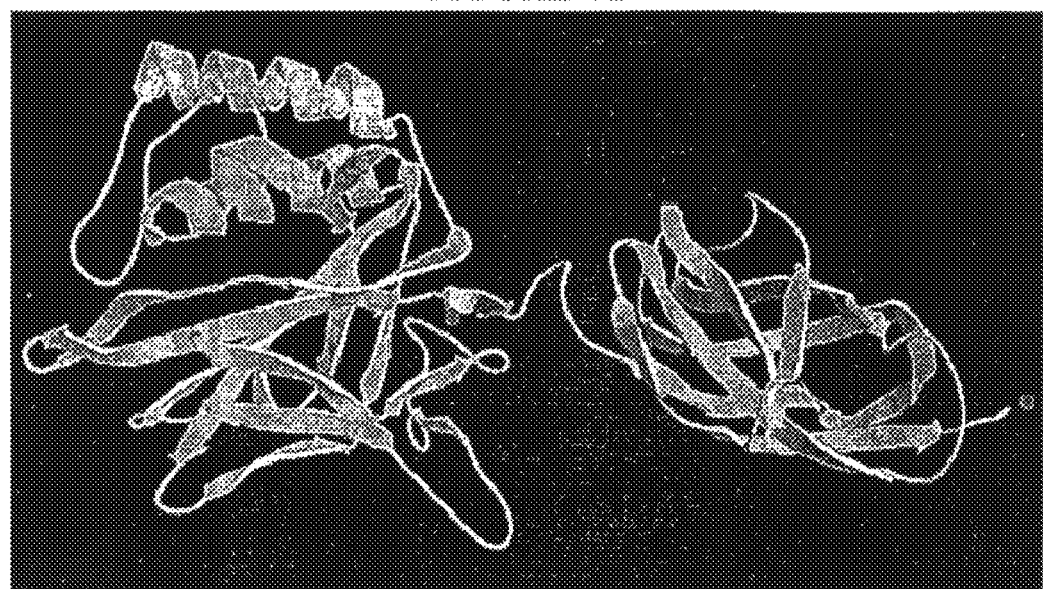
Terminus of truncated ORF
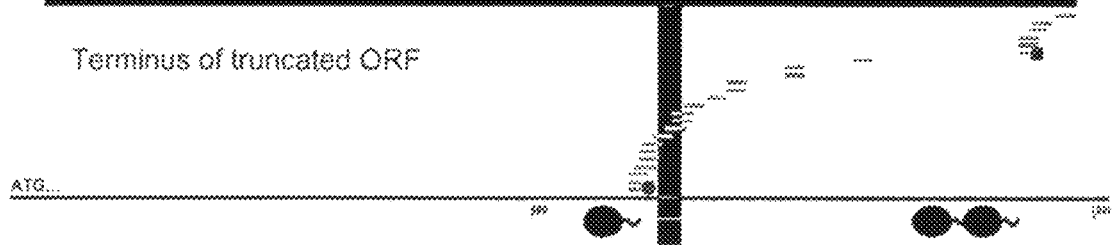
ATG...

METHOD FOR DETERMINING PROTEIN SOLUBILITY

This application is a U.S. national stage of International Application No. PCT/GB2005/003417 filed Sep. 5, 2005.

The present invention relates to methods of screening for expression of a soluble candidate protein within an expression library of candidate proteins. The method involves fusing each candidate protein in the library to a peptide substrate and identifying cells that express soluble candidate protein by detecting enzymatic modification of the peptide substrate.

All publications, patents and patent applications cited herein are incorporated in full by reference.

BACKGROUND TO THE INVENTION

Structural genomics has gained increasing interest in recent years. The elucidation of protein structures is important to enhance the understanding of protein function and thereby facilitate pharmaceutical drug development.

Protein expression and purification are key processes in such studies, and are often limited by the ability to produce properly folded recombinant protein. The preparation of proteins for structural and functional analysis using the *Escherichia coli* (*E. coli*) expression system is often hampered by the formation of insoluble intracellular protein aggregates (inclusion bodies), degradation by proteases or lack of expression.

*E. coli* is a common expression host that often makes misfolded protein when obliged to overproduce non-native gene products. This severely limits the usefulness of the protein in areas such as structural analysis by crystallography and NMR and limits the overall success rate of current structural genomics projects. Conventional approaches to problem of insoluble expressed proteins include low-temperature expression, the use of promoters with different strengths, a variety of solubility-enhancing fusion tags (Kapust R B & Waugh D S. '*Escherichia coli* maltose-binding protein is uncommonly effective at promoting the solubility of polypeptides to which it is fused'. *Protein Sci.* 1999 August; 8(8):1668-74) and modified growth media (Makrides S C 'Strategies for achieving high-level expression of genes in *Escherichia coli*'. *Microbiol Rev.* 1996 September; 60(3): 512-38. Review).

Another approach for overcoming this difficulty is through structure prediction from the amino acid sequence of the protein of interest. Information such as homology alignments and secondary structure prediction is used to predict the position of stable, soluble domains. A truncation or mutation of the target protein is first constructed and then expressed and tested for solubility. Despite continuous progress, the purely 'rational' design of proteins with desired properties, such as stability or soluble expression, is, at least to date, not generally feasible. Even in the presence of extensive structural and mechanistic information, it is difficult to predict the necessary sequence truncation required. There is still little information as to how amino acid sequence affects every aspect of protein structure, from its ability to be expressed in a heterologous host to its ability to fold in non-native environments. Experiments have demonstrated that changes in protein properties are brought about by the cumulative effects of many small adjustments, many of which are distributed or propagated over significant distances within the protein molecule and bioinformatic programs are currently unable to predict accurately which truncations or mutations will increase protein solubility.

In normal structural projects, several tens of clones may be constructed and tested for soluble protein expression. With such projects, the possible diversity is greatly undersampled and often solutions are not found. Additionally, with many proteins predicted from genome sequences there are no known homologues and this limits the effectiveness of bioinformatics approaches. High throughput screening strategies can prove effective for discovering soluble constructs when standard approaches fail. These require the accurate analysis of large numbers of expression clones to identify suitable constructs for structure determination. If the whole protein does not express or crystallise, the next step is to generate truncations or random mutations and retest.

Although (i) current methodologies permit the creation of very large expression libraries; and (ii) the chances that a library contains a soluble protein increases with the size of the library, the practical limits imposed by current approaches for screening expression libraries restricts this practice. The ultimate aim of experimenters who wish to express a soluble or crystallisable form of a protein of interest is to synthesise all possible variants of a target protein and screen them for soluble expression. Clones expressing soluble protein can be used directly, or can be used to seed the next round of library construction and selection. Such experiments would yield a massive number of clones, which would then have to be screened for the expression of soluble target protein.

Several systems have been described that have the aim of identifying soluble variants of a candidate protein of interest (generated by random mutagenesis or truncation). In fusion reporter methods, a candidate protein and a reporter protein with an easily detectable feature or biological activity are expressed as a genetic fusion. Information about the folding state of the protein can be derived from a screenable or selectable activity by the fused reported domain.

Fusion reporter methods usually involve fusion of a C-terminal partner "solubility reporter" (e.g. green fluorescent protein (GFP), Chloramphenicol acetyl transferase (CAT) or beta galactosidase. In the GFP fusion reporter method, the fluorescent yield of GFP provides information about the folding state of its fusion partner. Cells expressing GFP fused to a poorly folded insoluble protein fluoresce less brightly than those expressing GFP fused to a well-folded soluble protein. GFP monitors the folding yield of the test protein, which is subsequently expressed without the GFP tag (Waldo G S 'Genetic screens and directed evolution for protein solubility'. *Curr Opin Chem. Biol.* 2003 February; 7(1):33-8. Review).

The inventor has previously developed a fusion reporter system based on the use of biotin carboxyl carrier protein (BCCP) as a protein-folding marker. In this system, the biotinylation domain of BCCP from *E. coli* is fused to a test protein. The correctly folded secondary and tertiary structure of this domain is recognised by endogenous host cell biotin protein ligase which biotinylates the domain. Host cells expressing correctly folded test protein and BCCP domain will test positive for the presence of the biotin group (WO03/064656 'Protein tag comprising a biotinylation domain and method for increasing solubility and determining folding state').

However, there are problems associated with these systems, which limit their applicability.

The use of autonomously folding reporter proteins (e.g. GFP, CAT, beta-gal or BCCP domain) can generate problematic false positive rates due to their large and soluble nature. This can generate overwhelming false positive rates because the reporter can tolerate fusion of otherwise insoluble protein X fragments or full-length proteins without itself becoming insoluble. This may not be a problem when the tag can be left in place e.g. when immobilising proteins via the tag or performing biochemical analyses on the purified protein, but many applications e.g. protein crystallography, require removal of the tag by protease cleavage or genetic deletion; much time and expense is lost by processing clones that subsequently aggregate or degrade upon tag removal and are therefore unusable. It is also possible for the fusion protein to be degraded by proteolysis during expression in vivo, which leaves a soluble fluorescent reporter molecule that generates false positive results. These effects are very commonly observed with fusion proteins such as those containing maltose binding protein, glutathione-S-transferase, GFP, thioredoxin and is presumably a general effect. Thus, the presence of a highly soluble fusion partner acting as a solubility reporter strongly perturbs the solubility of what it is fused to.

Furthermore, most of the fusion proteins disclosed in the prior are large proteins. For example, fusion of GFP increases the size of the protein by approximately 37 kDa. Expression of large fusion proteins in $E.\ coli.$ is problematic, with a practical limitation of about 100 kDa.

Simulation studies, when combined with experiments and sequence/structure database analyses, can help delineate major evolutionary factors responsible for shaping proteins. However, the potential of such studies has not as yet been fully explored.

Accordingly, there thus exists a great need in the art for the development of a method for rapid, high throughput and reliable screening of the expressed proteins as early as possible in the overall process from cloning to structure determination, allowing the selection of soluble expressed proteins. Suitable methods should allow the high throughput screening of a large number of molecules containing different variant sequences, with the selection process allowing the easy identification of molecules with improved solubility. The amenability of such a method to the high throughput analysis of an expression library of variants of individual proteins, especially when used in combination with a mutation or truncation procedure strategy, to enable the identification and isolation of soluble variants of insoluble proteins would make the optimisation of high level expression of a problematic protein more affordable and less laborious. Additionally, the method should seek to i) minimise the pertubatory effects of any fusion partner and ii) should minimise the downstream steps required for structural analysis such as removal of the fused tag; proteins are routinely crystallised with small peptide tags but rarely as bidomain fusions.

SUMMARY OF THE INVENTION

This invention embraces mechanisms by which soluble variants of an insoluble protein may be selected. In these mechanisms the coding region of an insoluble protein can be manipulated, translated and expressed to determine whether a particular manipulation produces a soluble variant. Accordingly, the factors that affect the solubilization of the insoluble protein can be identified by sequencing of its encoding nucleic acid molecule. The mechanisms thus also give important insights into the protein features that impact on solubility.

According to one aspect of the invention, there is provided a method of screening for a soluble candidate protein within a plurality of variant candidate proteins wherein each candidate protein is fused to a peptide substrate such that a soluble candidate protein is identified by the detection of an enzymatic modification of the peptide substrate.

This novel method does not rely on the peptide substrate itself exhibiting some kind of testable activity, such as inherent fluorescence in the case of GFP or enzymatic turnover in the case of chloramphenicol acetyl transferase. The underlying principle behind the use of such a peptide as a solubility reporter is that only soluble molecules are efficient substrates for enzymes. Therefore, only if the peptide is fused to a soluble candidate protein, can it act as a direct substrate for an enzyme with no need for folding of the peptide itself. If, however, it is fused to an insoluble protein, its interaction with the peptide-modifying enzyme active site is severely restricted for steric and diffusional reasons and negligible enzymatic modification will occur resulting in a negative, unmodified phenotype. Additionally, if peptides are expressed in isolation in $E.\ coli$, (as would happen if fused out of frame to a gene or gene fragment) they are generally unstable, proteolysed and therefore removed from the cell, again resulting in a default negative phenotype. The method is amenable to the high throughput analysis of an expression library, for example, when used in combination with a protein truncation strategy. Because a large number of variants are made and tested in a single procedure, this greatly increases the chances of successfully identifying a soluble, and ideally highly expressed, candidate protein.

The peptide substrate is small and inert and thus does not significantly alter the physical characteristics of the candidate protein to which it is fused. In this case the term 'not significant', or variants thereof, in relation to an alteration of a physical characteristic means a variance of between +/−50% or less of the physical characteristic, for example +/−45% or less, +/−40% or less, +/−35% or less, +/−30% or less, +/−25% or less, +/−20% or less, +/−15% or less, +/−13% or less, +/−10% or less, or smaller. Preferably, the peptide substrate does not alter the physical characteristics of the candidate protein to which it is fused. Such physical characteristics include solubility, size, charge, folding and assembly mechanism of the candidate protein. A particular advantage is that the solubility of the candidate protein is neither perturbed nor enhanced. This limits the occurrence of false positive results, that are common in the methodologies of the prior art and are associated with the use of large, folded, soluble reporter molecules which will tolerate fusion of otherwise insoluble protein fragments.

A further advantage of the invention is that the methodology allows a quantitative analysis of the yield and solubility of candidate proteins to be made as well as a qualitative analysis. This allows a user to select clones encoding particularly soluble candidate proteins for analysis and/or further steps of manipulation and screening.

The term 'candidate protein' as used herein may be any protein or peptide, synthetic or naturally-occurring, including protein fragments, polypeptides, multimeric proteins, recombinant proteins, fusion and hybrid proteins, antibodies, and so on.

According to the invention a 'peptide substrate' includes any short region of peptide comprising amino acids joined to each other by peptide bonds or modified peptide bonds, i.e. peptide isosteres. This term refers both to short peptide chains of between 5 and 20 amino acids, as well as longer oligopeptide chains, of between 20 and 50 amino acids. Such peptides can be fused to a candidate protein and must be capable of functioning as a substrate for an enzyme, such that the peptide substrate becomes modified by enzymatic action when soluble.

Preferably, the peptide substrate is small in relation to the candidate protein to which it is fused. For example, in the case of large candidate proteins, is not so important that the size of the peptide substrate be diminishingly small, and slightly longer peptide substrates may be tolerated without perturbing the structure of the candidate protein and thus leading to false positive results. In contrast, in the case of small candidate proteins, the peptide substrate should ideally be as small as possible. Preferably, the length of the peptide substrate does not exceed 20% of the length of the candidate protein; more preferably, it does not exceed 15% of the length of the candidate protein; even more preferably, it does not exceed 10% of the length of the candidate protein; and even more preferably, it is less than 5% of the length of the candidate protein.

Preferably the peptide substrate is short, being 50 amino acids in length or smaller, for example, 45 or less, 40 or less, 35 or less, 30 or less, 25 or less, 20 or less, 15 or less, 13 or less, 10 or less, or smaller.

Preferably, the peptide substrate is linear and possesses no tertiary structure. By this is meant that the peptide does not fold into a structured, three-dimensional arrangement of secondary structure motifs.

Preferred peptide substrates include peptides that act as substrates for biotin protein ligase. One example of such a peptide substrate is the 15 amino acid peptide characterised by Schatz (1993) and Beckett et al. (1999) [Schatz P J (1993) Use of peptide libraries to map substrate specificity of a peptide-modifying enzyme: a 13 residue consensus peptide specifies biotinylation in *Escherichia coli Biotechnology*, 11 138-1143; Becket et al. (1999) A minimal peptide substrate in biotin holoenzyme synthetase-catalysed biotinylation Protein Science 8 921-929]. The sequence of this peptide is GLNDIFEAQKIEWHE (SEQ ID NO: 1) and several close variants also exist. When fused to a soluble protein, the peptide acts as a substrate for biotin protein ligase, an enzyme that transfers a biotin molecule from biotin-AMP to the lysine residue of this sequence that is underlined. When unfused, or fused to an insoluble partner, it is a very inefficient substrate. The use of peptide substrates that are substrates for biotin protein ligase allows proteins to be screened for solubility by detection with streptavidin conjugates. For example, a Western-type or dot-blot might be used in which streptavidin-peroxidase conjugates can be detected with chemiluminescence or directly using a fluorescently labelled streptavidin and a fluorimager instrument e.g. an Amersham Typhoon. Other compounds that are capable of binding to biotin include neutravidin, avidin and monomeric avidin.

Preferred peptide substrates also include peptides that act as substrates for a coexpressed kinase such as, for example, casein kinase II, a ubiquitous serine/threonine protein kinase found in eukaryotic cells. When fused to a soluble protein, the peptide (e.g. RRRDDDSDDD (SEQ ID NO: 2)) acts as a substrate for the kinase and becomes phosphorylated at a specific residue (S). As previously described, when unfused, or fused to an insoluble partner, efficient phosphorylation of the peptide does not occur. Phosphorylated peptide substrates are detected using a specific antiphosphoantibody. Binding of the antiphosphoantibody to the phosphopeptide may be detected directly e.g. using a flurocently labelled antiphosphoantibody conjugate.

As the skilled reader will appreciate, there are a number of ways in which the peptide substrate may be fused to the candidate protein. For example, the peptide substrate may be fused to the candidate protein by non-covalent bonds. The peptide substrate may be fused to the candidate protein post-translationally e.g. by intein biology. Preferably, the peptide substrate may be fused to the candidate protein by covalent bonds, for example, through a peptide bond, through chemical linkage and so on. Preferably, the peptide substrate is expressed as a genetic fusion, forming a recombinant fusion protein with the candidate protein. In cases of such genetic fusions, the attachment of the peptide substrate and the candidate protein components may preferably be achieved using a recombinant DNA construct that encodes the amino acid sequence of the fusion protein, with the DNA encoding the peptide substrate in the same reading frame as the DNA encoding the candidate protein.

The peptide substrate may reside either at the amino or carboxy termini of the candidate protein, or may be internal to the protein, for example, as a loop out of the candidate protein structure. Preferably, the peptide substrate is fused at the amino or carboxy terminus of the candidate protein.

According to the invention 'enzymatic modification' includes any modification of the peptide substrate which can be detected, for example by the binding of a marker or label, the addition or deletion of a chemical moiety from the peptide, a change of a chemical state such as phosphorylation, methylation, acetylation, ubiquitination, sumoylation, myristoylation or glycosylation. For example, with appropriate design of the peptide substrate, the change imposed by the modifying enzyme could activate the expression of an antibiotic resistance gene, allowing selection with antibiotics for the successful candidate, or activate the expression of a phenotypic marker gene, such as a gene encoding green fluorescent protein or beta-galactosidase, permitting a physical enrichment method such as FACS (fluorescent activated cell sorting). Preferably, the peptide substrate is biotinylated by enzymatic action. Other suitable types of modification will be clear to the skilled reader.

In an alternative embodiment, the peptide substrate may in some way affect the activity of the substrate modifying protein, for example, by acting as a co-factor for the enzymatic reaction, such that the activity of the substrate modifying protein is either raised or lowered specifically as a result of the solubility of the candidate protein. In this manner, if the candidate molecule expressed is soluble, the particular cell that encoded that candidate molecule may be isolated on the basis of the activity or inactivity of the substrate modifying protein, for example the complementation of an inactive mutant enzyme by a protein bearing a peptide that alleviates the effect of the mutation.

In the case of the preferred peptides for use in accordance with the invention, that are substrates for biotin protein ligase, the enzymatic modification is a change in the biotinylation state of the peptide.

In order for the enzymatic modification to take place, the presence of an enzyme is required that is capable of carrying out the required modification reaction. The enzyme may be added separately to the reaction mixture, or it may be endogenous to the reaction system, for example, being naturally expressed in a host cell in which the screening method is being carried out. For example, the cell may constitutively express the protein with activity as a substrate modifying substrate-modifying enzyme. In an alternative embodiment, the host cell may be transformed with an extrachromosomal element such as a plasmid, episome, artificial chromosome or the like, containing the polynucleotide sequence encoding the peptide substrate modifying enzyme.

According to the invention 'detection' refers to any suitable method that allows the identification of enzymatic modification of the peptide substrate has taken place. Once altered by an enzyme, the peptide tag must differ in some respect to allow its discrimination from unaltered peptide substrate. In this manner, soluble candidate proteins can be distinguished from insoluble candidate proteins. Suitable methods for the detection of modified peptide substrate will be clear to those of skill in the art and will, of course, depend on the property of the modifying enzyme that is being utilised. Detection may either be for altered peptide substrate, or unaltered peptide substrate. Preferably, detection is a positive detection for altered peptide substrate. For example, in the preferred embodiment of the invention that utilises a peptide substrate whose biotinylation state is altered, selection may be for this change in biotinylation state, and may exploit the high binding affinity exhibited by avidin and streptavidin for biotin, to allow detection on the basis of the high binding affinity of this binding pair. Alternatively, mass spectrometry can provide a method of detection of tag modification by monitoring a change in mass. With this detection method, no binding partner is required The screening of the candidate proteins of the invention may be carried out in vitro, using for example a cell-free translation system in which the candidate proteins are transcribed and translated without being expressed in cells. In this scenario, there must be some linkage between genotype and phenotype so that selection of soluble candidate proteins allows the concomitant selection of the encoding nucleic acid. This allows the deconvolution of the methodology so that the advantageous sequence features that led to the production of soluble protein can be assessed. Suitable methods are known in the art. For example, one in vitro system recently published in International patent application WO99/02671 reports the use of microcapsules created using water-in-oil emulsions to compartmentalise and thus isolate the components of a translation system.

Preferably, the candidate proteins are expressed in host cells. As the skilled reader will appreciate, any host cell system in which the candidate proteins are expressed will be suitable, including prokaryotic expression systems such as streptococci, staphylococci, *E. coli, Streptomyces* and *Bacillus subtilis* cells, and eukaryotic systems such as yeast (for example, *S. cerevisiae* and *Aspergillus* cells), insect cells, plant cells and mammalian cell cultures. *E. coli* is a preferred host cell for use in accordance with the invention, in part because it expresses an endogenous biotin protein ligase that thus allows modification of peptide substrates fused to candidate proteins within the host cell itself. One advantage of this mechanism is that the required link between genotype and phenotype is maintained within each cell and so the method allows analysis of the DNA sequence of candidate proteins found to be soluble. Other host cells that do not express biotin protein ligase compatible with this particular peptide can also be used, however, by introduction of the coding sequence for the enzyme into the cells before screening.

For expression in host cells, nucleic acid sequences encoding candidate proteins, optionally as fusion proteins with the peptide substrate, should be cloned into a suitable vector or vectors. The host cells may be transformed, transfected or transduced with such vectors to effect expression of the candidate proteins to be screened. Suitable expression methods are well known to those of skill in the art and many are described in detail by Sambrook et al. (supra) and Fernandez & Hoeffler (1998, eds. "Gene expression systems. Using nature for the art of expression". Academic Press, San Diego, London, Boston, New York, Sydney, Tokyo, Toronto). Generally, the encoding gene is placed under the control of a control element such as a promoter, ribosome binding site (for bacterial expression) and, optionally, an operator, so that the DNA sequence encoding the desired polypeptide is transcribed into RNA in the transformed host cell. The encoding nucleic acid molecule may include a sequence encoding a control sequence, such as a signal peptide or leader sequence, as desired, for example, for secretion of the translated polypeptide into the lumen of the endoplasmic reticulum, into the periplasmic space or into the extracellular environment. These signals may be endogenous to the polypeptide or they may be heterologous signals. Leader sequences can be removed by the bacterial host in post-translational processing. Preferably, the candidate protein is present in the same compartment of the cell as the substrate-modifying enzyme. For example, biotin protein ligase is a cytoplasmic protein and candidate proteins which are potential substrates for this enzyme should thus be retained in the cytoplasm. In addition to control sequences, it may be desirable to add regulatory sequences that allow for regulation of the expression of the polypeptide relative to the growth of the host cell.

The candidate protein can be recovered and purified from recombinant cell cultures for analysis, for example using well-known methods such as ammonium sulphate or ethanol precipitation, acid extraction and chromatography. However, some method must be used to allow the derivation of the recovered protein to be traced in order to retain the link between phenotype and genotype. More simply, the cells in which the candidate proteins are expressed may be lysed and analysed for modification of the peptide substrate. By recording the history of the colony from which a soluble candidate protein is derived retains the necessary link between genotype and phenotype. For example, in embodiments of the invention that screen for expression of soluble candidate proteins in host cells, the host cells can simply be lysed in situ on nitrocellulose membrane and tested for modification of the peptide substrate, for example, by blotting using antibodies, streptavidin or other detection reagents that recognise modified peptide substrate.

Specialised vector constructions may also be used to facilitate purification of proteins, as desired, by joining sequences encoding the polypeptides of the invention to a nucleotide sequence encoding a polypeptide domain that will facilitate purification of soluble proteins. Examples of such purification-facilitating domains include metal chelating peptides such as hexahistidine tags and histidine-tryptoplian modules that allow purification on immobilised metals, protein A domains that allow purification on immobilised immunoglobulin, and the domain utilised in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and the candidate protein may be used to facilitate purification. The biotinylated protein produced by biotin protein ligase may also be purified using avidin-derivatised agarose.

The vector can also include a functional selection marker. The functional selection marker can be, for example, a resistance gene such as kanamycin, ampicillin, blasticidin, carbenicillin, tetracycline, or chloramphenicol. The vector further can include a dysfunctional selection marker that lacks a critical element, and wherein the critical element is supplied by a nucleic acid element upon successful transformation of the cell with that element. The dysfunctional selection marker can be, for example, a resistance gene or a reporter gene, such as the lacZ gene, and the like.

These possible arrangements may, of course, be mixed so that some of the components of the reaction system are expressed from the genome of the organism and some are expressed from an extrachromosomal element, such as an expression vector.

In order to improve the chances of successfully selecting for soluble candidate protein, die reaction system should be incubated under conditions that are suitable for the activity of the peptide substrate-modifying protein. For example, in the case where an exogenous substrate modifying protein is added to a reaction medium, this medium should be placed under conditions suitable for the activity of the added protein. In cases where substrate-modifying protein is expressed in a host cell that is used in the screening methodology, the host cells should be grown under conditions suitable for their healthy growth and for die activity of the expressed protein. In such cases, there should be present in the system the appropriate transcriptional and translational machinery to allow expression of the substrate modifying protein from its encoding gene(s). This machinery will in most cases be derived from the cell itself.

The method allows the screening of a plurality of candidate protein variants. Indeed, one strength of the method is that it allows a very large number of different variants to be screened in parallel for activity. This means that it is possible, if desired, to perform an exhaustive screen for all or a very large number of possible variants of a particular protein or proteins, since the method is amenable to high throughput analysis.

Methods for the creation of libraries are well known in the art. For example, libraries of truncated genes can be constructed by Exonuclease III digestion (Ostermeir & Lutz, "The creation of ITCHY hybrid protein libraries", in Methods in Molecular Biology vol 231 pp 129-141).

For example, to identify a particular soluble variant for a protein that has proven difficult to solubilise, a library of truncations may be made. Such a library may contain, for example, progressive single or multiple amino acid truncations at either or both the N terminal and C terminal ends of die protein.

In a preferred embodiment, all possible truncations of a protein are made and tested. In order to be reasonably confident that an exhaustive screen has been performed, it will be necessary to over-sample each truncation by at least 3-fold, preferably at least 5-fold, more preferably 10-fold.

Truncation libraries may be incremental truncation libraries in which one end of the candidate protein is fixed and the other end varies. For example, the C terminus may be fixed and the N terminus varied, or the N terminus fixed and the C terminus varied. As an example of such a strategy, for a 770 amino acid protein, there are 670 truncations that leave a protein of greater than 100 amino acids in length (the approximate practical lower size limit for proteins expressed and screened in E. coli). At the DNA level, this corresponds to 2010 nucleotides. An over-sample of 10-fold will necessitate the construction and screening of 20,100 clones. One third of these clones will be in frame whilst two thirds will contain a frameshift and therefore not express a useful peptide-tagged protein.

Truncation libraries may be internal fragment libraries in which the candidate proteins have been truncated at both ends. This circumvents the scenario in which a particular fixed terminus causes some unexpected and unpredictable problem, for example, an expression problem, which thus leads to biased or useless results e.g. susceptibility to cellular proteolysis or toxic interaction with the cell. For a particular protein of "N" residues, approximately $N^2/2$ fragments will exist. To ensure that the protein coding sequence is in the correct orientation and in-frame at both ends requires an 18-fold over-sampling. Taking the example of a gene encoding a 500 amino acid protein, this yields 2 million possible ligation products; a 10-fold over-sample thus means that a library of 20 million clones must be sampled.

Methods for truncation will be known to those of skill in the art. The simplest way to effect truncations of this type is to use the various well-known techniques of genetic engineering to delete selectively the encoding nucleic acid sequence at either or both ends, and then insert the desired coding sequence into the vector of choice. Preferably, truncations of the candidate protein are created using 3' and/or 5' exonuclease strategies selectively to erode the 3' and/or 5' ends of the encoding nucleic acid, respectively. One preferred technique for the generation of truncation libraries is to use controlled or random exonuclease III digestion of nucleic acids, preferably combined with the use of restriction enzyme digestion. For example, certain restriction enzymes cut at sites that leave 3' overhangs (e.g. NsiI). Others cut at sites that leave 5' overhangs (e.g. Not1). By cutting at one of the other of these sites, and using either 3' and/or 5' exonuclease enzymes, and incubating the reaction for controlled periods of time, a selective degree and direction of digestion can be achieved. Examples of suitable vector constructions that are suitable for use with the method of the present invention are described in the Examples contained herein. Alternatively, PCR amplification of the target gene using random primers can be used to generate gene fragments truncated at both ends (Kawasaki et al, Random PCR-based screening for soluble proteins using green fluorescent protein, *Biochem. & Biophys. Res. Comm.* 2001 vol 280 pp 842-844). Other equivalent methods include DNAseI digestion, sonication and point sink fragmentation.

A library of variants may be made in which mutations have been made. Mutagenesis may be random mutagenesis, or may be rational, site-directed mutagenesis. Suitable methods of manipulation will be known to those of skill in the art and include point mutagenesis (error-prone PCR, chemical mutagenesis, the use of specific mutator host strains), recursive ensemble mutagenesis (Delagrave and Youvan (1993) Bio-Technology, 11: 1548-1552), combinatorial cassette mutagenesis (Black et al., 1996), DNA shuffling (Stemmer et al., 1994) or by codon substitution mutagenesis. For a review of recent improvements in processes for in vitro recombination, see Giver and Arnold, 1998 (*Current Opinion in Chemical Biology*, 2(3): 335-338). For example, a particular amino acid or acids might be selectively mutated from the wild type sequence to other amino acids. Such mutants may include variant candidate proteins in which one or more of the amino acid residues are substituted with a conserved or non-conserved amino acid residue (preferably a conserved amino acid residue). For example, residues of high conformational flexibility such as Arg or Lys might be exchanged for those of low entropy such as Ala with the aim of improving the homogeneity of crystallisation in order to achieve better quality protein crystals for X-ray analysis. Such substituted amino acid residue may or may not be one encoded by the genetic code. Typical such substitutions are among Ala, Val, Leu and Ile; among Ser and Thr; among the acidic residues Asp and Glu; among Asn and Gln; among the basic residues Lys and Arg; or among the aromatic residues Phe and Tyr. Particularly preferred are variants in which several, i.e. between 5 and 10, 1 and 5, 1 and 3, 1 and 2 or just 1 amino acids are substituted, deleted or added in any combination. Especially preferred are substitutions, additions and deletions which do not alter the functional properties or activities of the protein. Also especially preferred in this regard are conservative substitutions. Such mutants also include polypeptides in which one or more of the amino acid residues includes a substituent group.

A library of variants may be made in which insertions have been added to the sequence, for example, of one or more amino acids, or a run of amino acids so as, for example, to form or delete a loop in the candidate protein. Particularly if hydrophilic amino acids are included, an enhancement of the solubility of the candidate protein may result.

These libraries of candidate proteins are then screened for the particular variant(s) that exhibit the greatest degree of solubility.

According to this aspect of the invention, a library of candidate proteins may contain more than $10^3$ different clones, more than $10^4$ different clones, more than $10^5$ different clones, more than $10^6$ clones, more than $10^7$ clones, more than $10^8$ clones or even more. Preferably, the library contains clones expressing every possible truncation and variant of the candidate protein. This is advantageous because the creation and testing of all possible truncations greatly increases the chances of success and allows for the analysis of large amounts of data which can be used to link variations in solubility to features of the protein sequence. Furthermore, a comprehensive screen of all positions allows an experiment to be confidently abandoned should only negative results be obtained.

A library of clones may comprise a plurality of transformed cells, each cell of which expresses a different candidate protein. Such a library can be created by transforming a preparation of cells with a library of suitable vectors. Under the appropriate conditions, transformation with such vectors may be performed so as to ensure that substantially only one type of candidate protein is expressed in each cell of the library. This confines the proteins that are expressed from that nucleic acid within the same cell and facilitates the selection of nucleic acids encoding molecules of interest; were each cell to include multiple nucleic acid molecules, then upon isolation of the cell it would not be clear which nucleic acid molecule had encoded the protein that caused the desired effect.

The improved selection techniques that form part of the invention permit the simple use of reiterative molecular evolution cycles so that large pools of potential candidates can be carried through a series of repetitions. Preferably, a clone expressing highly soluble candidate protein will be obtained from the library of clones without the need for any further manipulations. However, in order to optimise the solubility of a candidate protein that has been identified as soluble by the method of the invention, it may be necessary or desirable to perform reiterative steps of sequence alteration and screening. For example, the screening of an initial library may select a number of candidates with increased solubility, although this library will be predominantly contaminated with clones expressing insoluble or non stably-expressed protein. However, reiterative cycling, using soluble candidates selected after the first round of screening to parent a next generation of candidates allows the process to be repeated; it may be possible to evolve these soluble candidates further toward solubility by performing additional steps of sequence alteration and screening. The content of the pool will increasingly become populated by more soluble ("fitter") candidates. After a series of reiterative cycles, the pool of successful candidates can be taken and manipulated to create a new library that is used to start a new series of reiterative cycling under a more stringent selection criterion. Preferably, only one iteration of the manipulation and screening steps is performed, more preferably three, still more preferably four or more. The possibility of automation may allow the use of many more cycles, perhaps exceeding 100, 500 or 1000, if necessary.

In order to use the methodology of the current invention to its full potential in a high throughput screening methodology, it is necessary that the screen can function on a scale commensurate with the size of the library. To fully exploit the potential of this type of technology, the use of a colony picker and arraying robot should be used to convert plated transformants into an ordered library and screen these for positive colonies. Ideally, each colony is given an "address" that corresponds to a particular well in a plate. The use of barcodes can facilitate this. Optionally, the library can be replicated exactly for security. Preferably, the screening and selection of colonies is automated, using video technology combined with a 96 pin picking head and the like. 384 well plates can accelerate the process by allowing more colonies to be screened. Using this technology, an approximate picking rate of 2500 colonies per hour is easily achieved.

In a preferred methodology for putting the method of the invention into effect, a library of transformants are arrayed as inocula onto nitrocellulose membranes over LB agar, resulting in colony arrays (Buessow et al, 1998 *Nucleic Acids Research* Vol 26, pp 5007-5008). Expression of the proteins is induced, for example, by shifting the membrane onto agar containing IPTG and biotin and growing the cells for around 3 hours at a suitable temperature. The cells are then lysed in situ. A large-scale dot blot analysis can then be performed for protein and/or DNA content. In this way, 60,000 clones can be arrayed and tested per 22×22 cm membrane. Using such an assay format has advantages over expression of clones in microtiter plates since the colonies themselves act as expression vessels and the logistics of expressing and testing so many clones are greatly simplified. If arranged in a readily deconvolutable geometric array, quantitation of expression levels and solubility levels is facilitated by use of array analysis software; clones can be ranked for expression level and prioritised. The method allows easy, parallel processing of large numbers of assay points and simple tracking of assay data back to the physical original clone. Such processing is preferably software-controlled.

In this type of methodology, cellular proteins from the arrayed colonies are deposited oil the membrane after in situ cell lysis by placing the membrane with colonies on a sodium hydroxide-soaked pad. The proteins can be detected by an antibody against the tag which is insensitive to the post translational modification (e.g. biotinylation) and this permits assessment of protein yield although does not indicate the solubility status of the protein. More importantly, the protein can be detected using a detection method that is sensitive to the solubility status of the clone e.g. in the case of post-translational biotinylation of the protein indicating solubility, streptavidin binding provides a readout on whether the tag has been modified. Additionally, useful information on expression conditions can be achieved by comparison of the antibody and streptavidin signals, e.g. in an XY scatter graph, thereby permitting an estimation of the fraction of total protein that is soluble. If the streptavidin is conjugated to a peroxidase or alkaline phosphatase, the detection can be by chemiluminescence or conjugated to a fluorescent dye, visualisation can be by fluorescence imaging. Clones identified as biotin positive can then be isolated from the library and tested in conventional ways to verify soluble expression. Thus a clone exhibiting a biotin positive phenotype can be grown in liquid culture, protein expression induced by addition of IPTG and the solubility status confirmed by lysis and subsequent fractionation of the lysate into insoluble and soluble preparations e.g. by centrifugation or filtration.

Proteins can then be analysed and characterised, such as by SDS-PAGE and western blot. A comparison of replicate membranes probed with antibody and streptavidin thus permits a readout of the solubility status of a particular variant e.g. truncation, as being expressed or not expressed, soluble or insoluble. In this way an "expression map" can be generated permitting measurement of the effects of truncation at single amino acid resolution. This is the type of information that structural biologists require when designing constructs for protein expression and may lead to a deeper understanding of factors affecting protein expression.

In more detail, clones can be sequenced to identify the exact identity of the truncations and to identify junctions and replicates. Using these data, clones can be prioritised by expression level and size to from the information contained in a soluble expression map (FIG. 6) that correlates the solubility of the construct against the truncation point in the encoding gene sequence. As can be seen from FIG. 6, there is a degree of order evident from portraying the degree of solubility of the various clones ranked according to the sequence of the encoding gene. Similar levels of solubility are evident in constructs with consecutive truncations (see straight lines drawn through marker points), and these are believed to correspond to regions of consecutive residues in solvent-exposed linkers. In contrast, gaps of poor solubility are evident from truncation boundaries that fall within structured regions in the protein (see region marked as "binding domain" in FIG. 11). It is hypothesised herein that this type of analysis allows an exhaustive analysis of the solubility of truncated variants of a protein to divulge information on protein structure, such as domain boundaries, and the degree of solvent exposure of residues in the primary structure of the protein. Thus, in a further aspect, the invention provides a method for obtaining information relating to protein structure, the method comprising performing a method of screening according to any one of the embodiments of the invention described above, and correlating information regarding the solubility of each construct with the truncation point in the protein sequence. Preferably, the data obtained from the any one of the embodiments of the invention is used to create a soluble expression map by plotting the solubility of the construct against the truncation point in the encoding gene sequence. Solvent-exposed linker regions are identified as regions of consecutive residues with significant solubility. Gaps between solvent-exposed linker regions are identified as structured regions in the protein sequence. Inflexion points between the solvent-exposed residues and the structured regions are identified as domain boundaries within the protein sequence.

Prior to expression testing in the array format above, the quality of the gene truncation libraries should be measured by analysis of the distribution of sizes of gene fragments. Such characterisation will typically involve a PCR screen with primers that flank the insert. This gives an idea of the size of the insert. The start codon can then be confirmed by digesting the PCR product using a restriction enzyme that includes ATG in its recognition site (e.g. NdeI). Following expression-testing in the array format and isolation of positives from the library, clones can be sequenced to identify the exact identity of the truncations.

In conjunction with the methodology described above, suitable controls should preferably be used to ensure that false positive and false negative results are taken into account. For example, a positive control should use a protein that is known to be soluble under the conditions used for the screening.

An example of a positive control might be maltose-binding protein (MBP) to which the peptide substrate is fused. This protein is solubly expressed and thus experiences modification of the peptide substrate by the substrate modifying protein. In the embodiment of the invention that utilises a biotinylation peptide fused to the candidate proteins, a positive control clone would thus be MBP fused to the biotinylation peptide. A negative control might be, for example, a clone containing a frameshift in the peptide-encoding sequence such that the peptide is either not expressed or is expressed but not fused to a soluble protein. An alternative, and optionally complementary negative control clone might encode an insoluble protein in frame with the peptide. Being insoluble, the peptide will not act as an efficient substrate for the substrate modifying protein.

Further aspects of the invention relate to kits for use in accordance with the methodology described above. For example, a suitable kit for identifying soluble variants of a candidate protein may comprise:

a) an expression vector for expression of variant candidate proteins in a host cell; wherein said vector contains restriction sites to allow insertion of a gene of interest encoding the candidate protein such that a sequence encoding a biotinylation peptide is fused genetically to the gene of interest;

b) a positive control vector that expresses maltose binding protein genetically-fused to nucleic acid encoding the biotinylation peptide;

c) a negative control vector as in b) but which includes a frameshift in the biotinylation peptide encoding sequence so the maltose binding protein is not biotinylated; and d) a further negative control vector that expresses an insoluble protein in frame with the biotinylation peptide.

The kit may also contain instructions for generating truncation libraries of genes encoding a candidate protein of interest and cloning the truncations so that they are fused to sequence encoding the peptide substrate.

Various aspects and embodiments of the present invention will now be described in more detail by way of example. It will be appreciated that modification of detail may be made without departing from the scope of the invention.

BRIEF DESCRIPTION OF THE FIGURES

FIG. 12: Alignment of solubly expressing NF-κB constructs identified by random screening with the predetermined, full-length protein structure. High-resolution definition of domain boundaries is apparent from the clones marked with a dot. These are the most compact forms of the 1- and 2-domain constructs.

RESULTS & METHODS

Examples

Proof of Concept of Methodology Applied to a 1) a Candidate Gene encoding a previously unexpressed protein and 2) the Human NF-kappa B gene encoding a protein of known structure for validation purposes Construction of Vectors Allowing Analysis of N-Terminal Truncations of Proteins Encoded by the Inserted Gene of Interested.

A plasmid for general usage in solubility screening was initially constructed by assembling a vector containing a gene of interest together with relevant features enabling the truncation process. This initial construct was used in the analysis of the candidate gene, but also as the source of plasmid for cloning any other gene of interest by direct, simple replacement of the candidate reading frame for another. The construction of the candidate gene-containing construct is described followed by that of a derivative construct containing a different, unrelated gene, NF-kappaB.

a) PCR of the Candidate Gene

The candidate gene was cloned by PCR from a previous plasmid containing the open reading frame. PCR reactions were performed in 50 ul reactions using PWO polymerase (Roche) according to the instructions provided. The PCR construction used 4 oligonucleotides primers in a strategy whereby small outside primers amplified the initial amplicon produced by priming of the large oligos (to increase efficiency of the reaction):

60 nM for 1

[5'GATCCTAGCATATGAAATGCATGGATC-CGCGGCCGCTGAXXXXXXX-3' (SEQ ID NO: 3)] where X indicates a complementary base to the candidate gene sequence omitting the ATG start codon, 600 nM for 2 [5'-GATCCTAGCATATGAAATGCATGG-3' (SEQ ID NO: 4)],

```
60 nM Fselrev1
[5'-GATCCTAGGGCCGGCCXXXXXXXXXXXXXXXXXXXXXXXX

XXX-3' (SEQ ID NO: 5)]
and 600 nM Fselrev2
[5'-GATCCTAGGGCCGGCCXXXXX-3' (SEQ ID NO: 6)]
```

PCR conditions were 94° C., 2 min and then 25 cycles of 94° C., 30 sec; 45° C., 30 sec; 72° C.; 2 min.

The PCR was electrophoresed on 1% TBE agarose, the bands excised and DNA products purified using a QIAEXII kit (Qiagen) To generate insert for cloning, 1 ug of the PCR product was digested to completion with NdeI and FseI and the 2230 bp DNA fragment then gel purified by QIAEXII.

b) Construction of a Vector Containing DNA Encoding the Biotinylation Peptide and Suitable Restriction Sites for Cloning the Candidate PCR Product An oligonucleotides cassette was generated by annealing two oligos

```
biot-1_for
[5'-AGCTTGCTTGGTGGCGGTCTGAACGACATCTTCGAGGCTCAGAAAA

TCGAATGGCACGAATAATGAG-3' (SEQ ID NO: 7)]
and biot-1_rev
[5'-AGCTCTCATTATTCGTGCCATTC-
GATTTTCTGAGCCTCGAAGATGTCGT

TCAGACCGCCACCAAGCA-3' (SEQ ID NO: 8)].
```

This was ligated into the HindIII site of pMAL-c2g [New England Biolabs] forming the intermediate plasmid pMAS 103 which was then digested with NdeI and FseI. The 5521 base pair fragment (the vector backbone) was gel purified as above and dephosphorylated with Shrimp Alkaline Phosphatase (Amersham).

c) Cloning of the PCR Product into an *E. coli* Expression Vector

Figure 1:
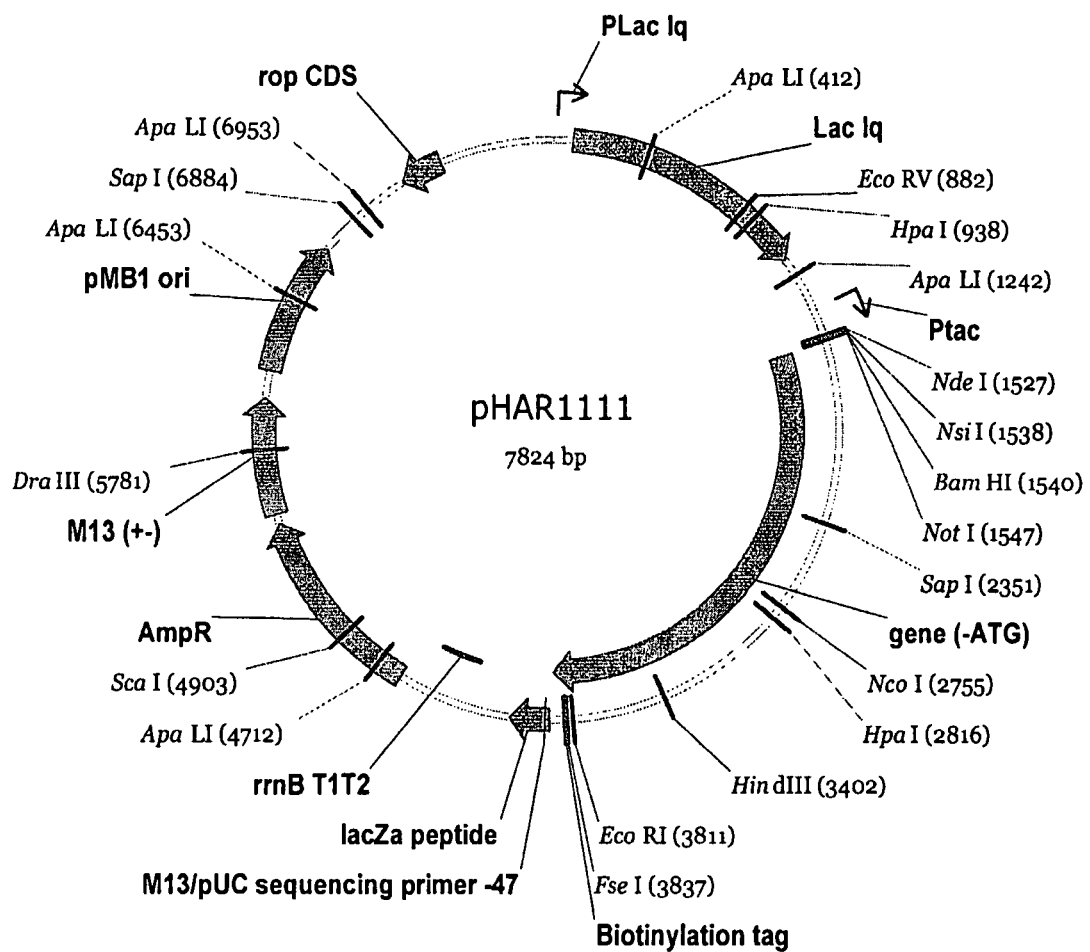
FIG. 1: Plasmid pHAR1111 encoding a candidate gene fused in frame at the 3' end to DNA encoding a biotinylation peptide and with restriction sites at the 5' end of the gene designed to permit fabrication of a N-terminal truncation series of the protein.

The 2230 base pair candidate gene insert was then ligated to the 5521 base pair pMAS103-derived backbone with T4 DNA ligase (Rapid Ligation Kit, Roche) and the reaction was subsequently desalted using a PCR Quick column and eluted in 35 ul of 10 mM Tris Cl pH 8.0. The *E. coli* strain DH5alpha was transformed by electroporation with the 2 ul of desalted ligation reaction, recovered for 1 hour in SOC medium and plated on LB agar supplemented with ampicillin to 70 ug/ml. Plasmids were isolated from several colonies and were characterised by restriction digest and DNA sequencing to confirm the correctness of the construction: pHAR1111 (see FIG. 1).

Plasmid pHAR1111 was used in a gene truncation experiment for the candidate gene. It was also used as a starting vector for analysis of other genes: the candidate gene was excised by plasmid digestion with NotI and FseI and alternative genes inserted by ligating genes with compatible NotI and FseI sites, introduced by PCR, at equivalent positions relative to the start and stop codons of the open reading frame.

Figure 2:
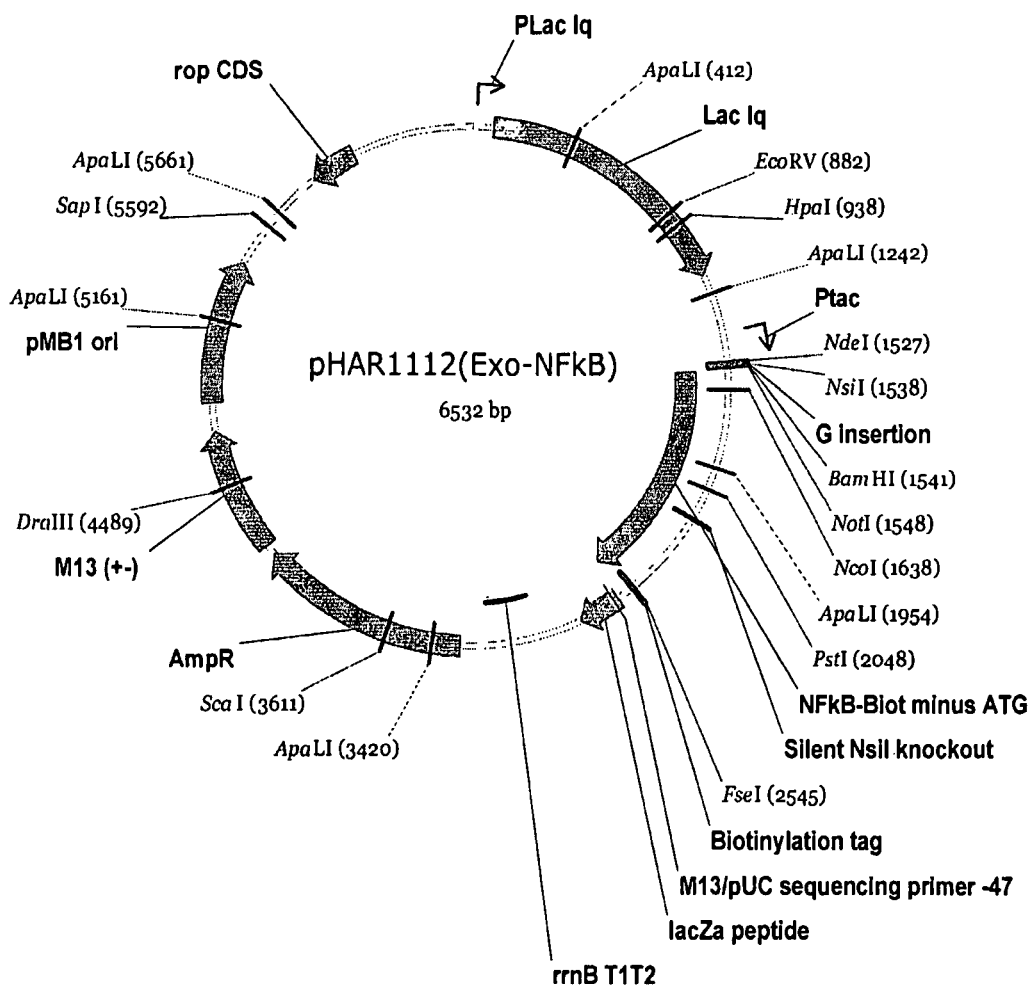
FIG. 2: Plasmid pHAR1112 encoding the human NF-kappaB gene fused in frame at the 3' end to DNA encoding a biotinylation peptide and with restriction sites at the 5' end of the gene designed to permit fabrication of a N-terminal truncation series of the protein.

For example, the human NF-kappaB gene was initially mutated to silently remove an internal NsiI site. It was then amplified by PCR with oligonucleotides primers NFkBfor1 [5'-GGATCCGCGGCCGCTGAGCAGATGGC-CCATACCTTCAAATATTAGAGC-3' (SEQ ID NO: 9)] and NfkBFseRev1 [5'-GGGATCCGGCCGGCCCCTTCT-GACGTTTCCTCTGCACTTCTTC-3' (SEQ ID NO: 10)] resulting in a gene in which the original start codon had been removed. The PCR product was digested with NotI and FseI and ligated in to vector backbone derived by NotI and FseI digest of pHAR1111. Thus the NF-kappaB gene was generated in a form compatible with N-terminal deletion of the protein encoded by the gene (vector pHAR1112; FIG. 2).

In summary, two similar vectors were produced permitting 5' deletion libraries to be made: pHAR1111 contained a previously unexpressed candidate gene; pHAR1112 contained the gene for the transcription factor NF-kappa B, a protein of known structure that could be used for validation purposes.

d) Construction of Vectors Allowing Analysis of C-Terminal Truncations of Proteins Encoded by the Inserted Gene of Interest.

The vector pMAS103 (described above) formed the basis of a second construct enabling digestion at the 3' end of the gene of interest. Here candidate genes were cloned full-length as DNA fragments in which the start codon (ATG) is present in an NdeI site (CATATG) and where the stop codon is followed by any form of end compatible with the BamHI, XbaI, SalI or HindIII sites of the pMAS103 vector (either as compatible overhang or by blunt-end ligation).

To exemplify this, the Human NF-kappaB gene was excised by NdeI and BamHI digest from another plasmid (pHAR307) that contained the gene fused to DNA encoding a C-terminal hexahistidine tag (the tag has no significance in this experiment). This fragment was ligated to pMAS103 vector backbone prepared by digestion with NdeI and BamHI.

Figure 3:
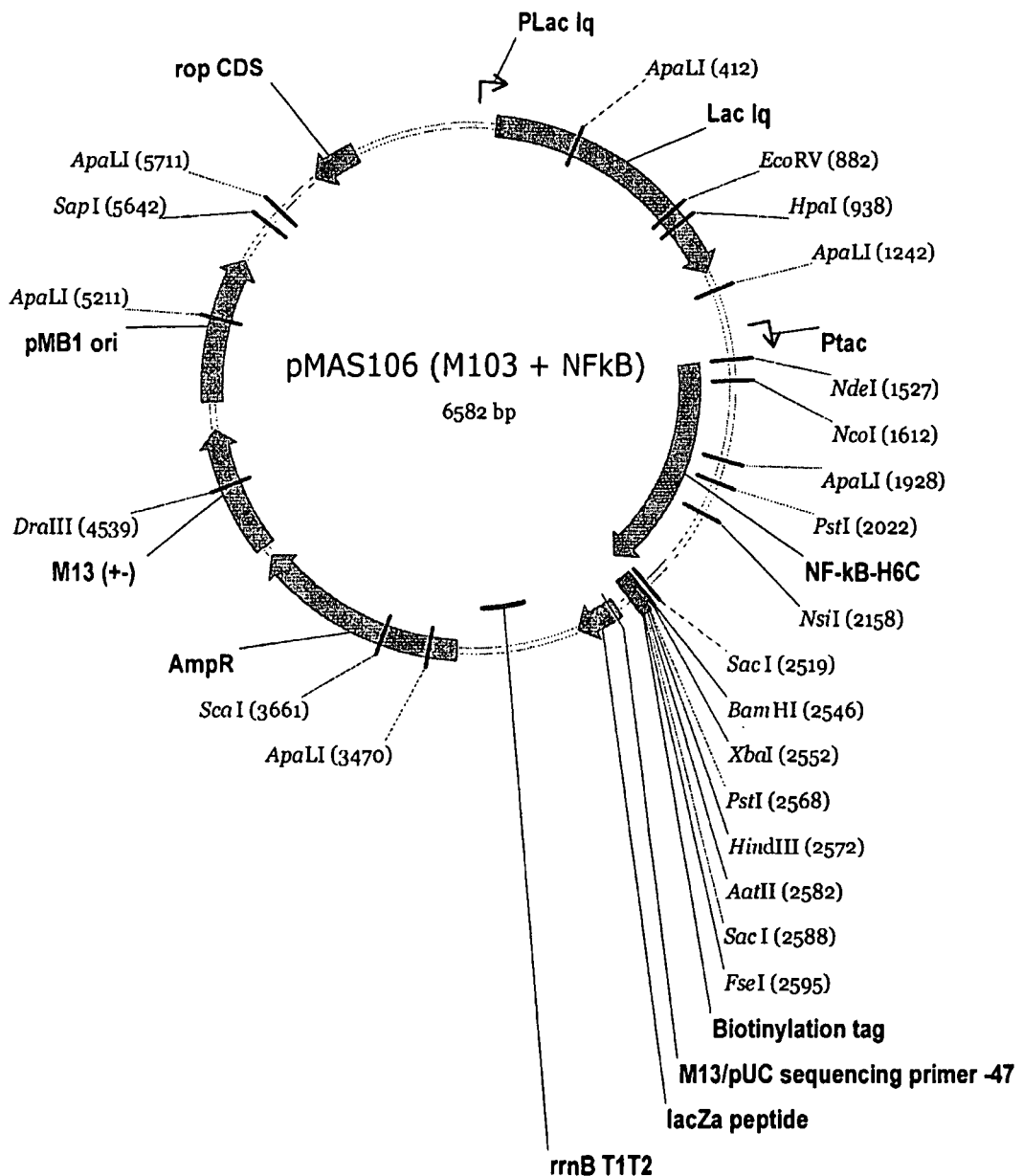
FIG. 3: Plasmid pMAS106 encoding the human NF-kappa B gene in frame at the 5' end adjacent, but not in frame with DNA encoding a biotinylation peptide at the 3' end and with restriction sites at the 3' end of the gene designed to permit fabrication of a C-terminal truncation series of the protein.

In summary, the plasmid, pMAS106 (FIG. 3) contains the NF-kappaB insert in a form compatible with C-terminal deletion of the protein encoded by this gene. This was subsequently used for validation purposes since the protein structure of NF-kappa B is well-characterised.

Truncation Protocol (Described for the Vector pHAR1111 Containing a Gene for a Previously Unexpressed Protein)

The truncation protocol was performed according to the ITCHY method (see The Creation ITCHY Hybrid Protein Libraries in Methods in Molecular Biology by Ostermeier, M. & Lutz, S., vol 231, pp 129-141). Briefly, in order to enzymatically truncate the gene of interest, 10 micrograms of plasmid pHAR1111 was digested to completion with NotI and NsiI. 4 micrograms of purified, linearised vector was diluted in 1× buffer 1 (New England Biolabs), 80 mM NaCl (in addition to that in the buffer) and in a final volume of 120 microliters. Immediately, 30 microliters was removed in to 150 microliters of PB buffer (Qiagen) forming a t=0 sec control. To the remaining 90 microliters at 22° C., 150 units of Exonuclease III was added and mixed. At 30 second intervals, 0.5 microliters of the enzyme-DNA reaction was removed and added to a single "quenching tube" comprising 300 microliters of PB buffer on ice. This was continued for a total of 1 h until 90 microliters of the reaction mix had been transferred. The remaining 30 microliters formed the t=1 h control and was also added to 150 microliters of PB buffer. The three reactions (t=0, t=1 h and the library) were cleaned up using PCR cleanup spin columns (Qiagen) and eluted in 30 microliters, 30 microliters and 50 microliters of EB buffer respectively). The control samples were analysed on gel to verify the exonuclease reaction (data not shown)

In order to remove the single stranded overhang left after the exonuclease digest, the 50 microliters of library mix was diluted in 1× Mung Bean Nuclease (MBN) buffer (New England Biolabs) and 3 units of MBN enzyme added in a final volume of approximately 55 microliters. The reaction was then incubated at 37° C. for 30 mins. The reaction was cleaned up using PCR cleanup spin columns and eluted in 65 microliters of EB.

To polish the ends of the vector prior to ligation, 48 microliters of the library DNA was diluted in 1× T4 DNA polymerase buffer (New England Biolabs) with 2.5 mM dNTPs and 1 unit of T4 DNA polymerase in a final volume of 100 microliters. The reaction was incubated at 12° C. for 20 min and then quenched by addition of EDTA to 10 mM final concentration and heating to 75° C. for 20 min.

The reaction mix was loaded onto a 0.5% TBE agarose gel and electrophoresed to separate DNA fragments by size. DNA in the size range of interest (>5.5 kilobases) was excised from the gel, purified using QIAEXII resin (Qiagen) and eluted in 60 microliters of EB.

The size-selected DNA corresponding to linearised vector containing truncated gene fragments was the recircularised by ligation with T4 DNA ligase by incubating 8 microliters of DNA solution from the QIAEXII purification with reagents from the Roche Applied Science Ligation Kit according to the manufacturer's instructions. The ligation mix was desalted using a PCR cleanup spin column and 2 microliters was used to transform E. coli DH5alpha competent cells by electroporation. After recovery of the transformation mix in SOC media, the library was plated out on 22 cm square agar plates (Genetix, UK). After overnight growth at 37° C., approximately 24, 000 colonies were scraped from the agar, resuspended in PBS and plasmid prepared from a small aliquot of cells using a miniprep kit (Qiagen). This plasmid was used to transform the protein expression strain of E. coli, BL21 Codon Plus RIL (Stratagene). The even size distribution of truncations was confirmed by a colony PCR screen of 96 clones with flanking primers and agarose gel electrophoresis.

Robotic Handling of Library.

Colony Picking

The BL21 Codon Plus RIL transformed with the plasmid library was plated out on 22 cm square LB agar plates (ampicillin 70 mg/l; chloramphenicol 30 mg/l) at a density of approximately 4,000 colonies per plate grown at 30° C. 26,880 colonies were robotically picked, using a Kbiosystems gridder-picker robot, into 384 well plates filled with 70 microliters LB-HBFM medium per well (supplemented with ampicillin and chloramphenicol). Liquid cultures were grown overnight to saturation at 30° C. in a HiGro shaker incubator (Genomic Solutions).

Gridding onto Membranes

Figure 4:
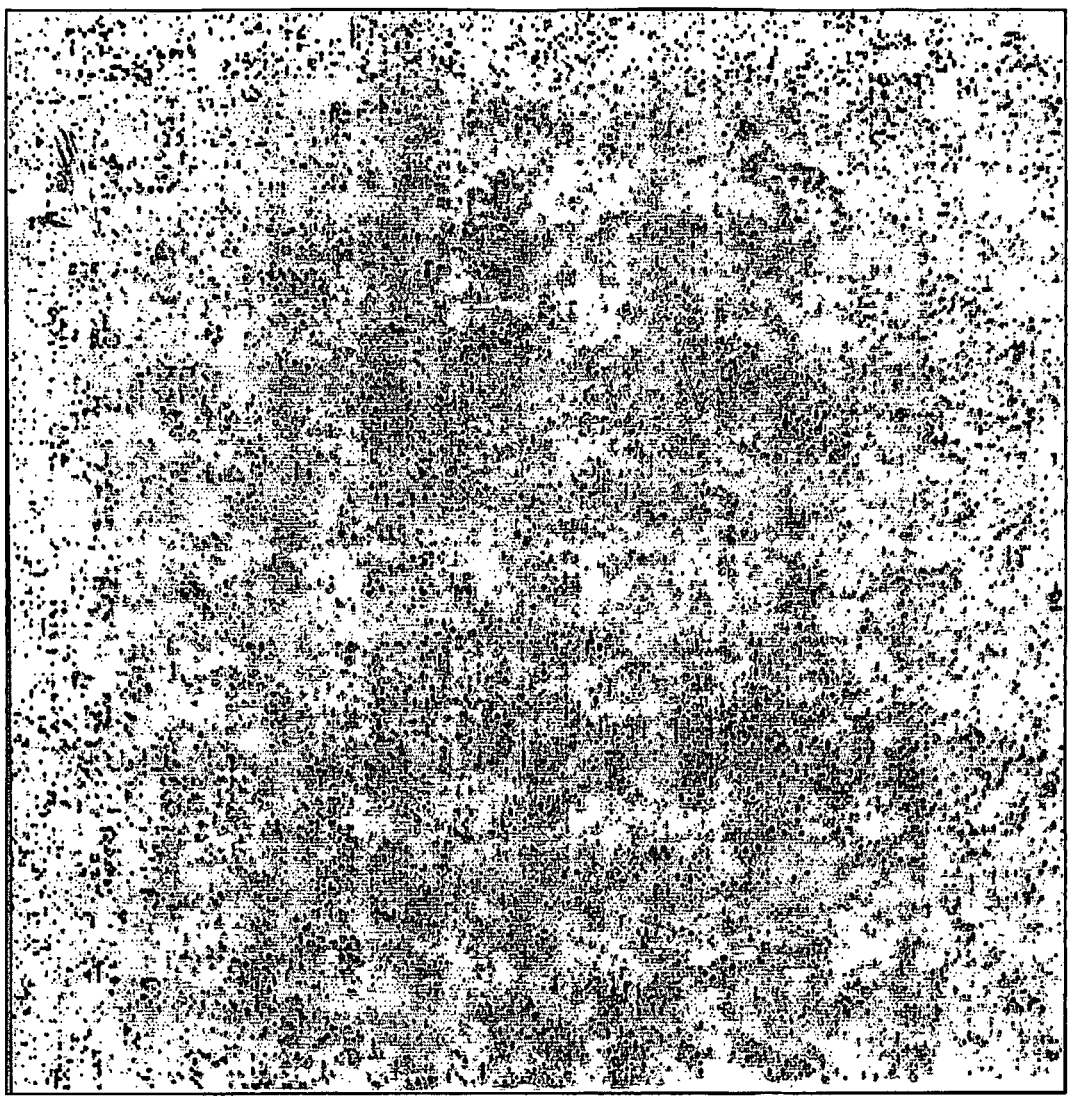
FIG. 4: Expression analysis. Picture 1a shows the full array probed with an antibody to the peptide tag after immediate lysis. Total expression (not soluble expression) is apparent.

Squares of nitrocellulose membrane (Amersham) were cut and laid on the top of 22 cm LB agar plates (supplemented with ampicillin and chloramphenicol). Using a gridding pin tool and the arraying robot, the cultures were printed on to the membranes at high density. Plates were then incubated overnight at 25° C. until colonies were just visible to the naked eye. The membranes were lifted from the agar and laid over fresh LB agar plates (supplemented with ampicillin and chloramphenicol) that were supplemented with IPTG at a final concentration of 0.1 mM to induce recombinant protein expression within the colonies. Immediate lysis and detection of the full array with antibody against the biotinylation peptide at this point leads to the detection of clones which express protein (either soluble or insoluble; FIG. 4). Membranes were incubated for 4.5 h at 30° C., lifted from the inducing agar and placed at minus 80° C. Prior to analysis, the membranes are warmed to room temperature and laid over filter paper soaked in 0.5M NaOH, 1.5M NaCl for 10 mins at room temperature. The membranes are then neutralised with 2×5 min in 1M Tris HCl, pH7.5; 1.5 M NaCl and then for 15 min in 2×SSC buffer. The membrane was then blocked overnight with Superblock (Pierce).

Hybridisation with Streptavidin and Antibody Against Peptide Tag

Detection of Expressed Proteins

A mouse monoclonal anti-avitag antibody (Avidity) was diluted 1:7,500 in 40 ml of PBS-T and added to the membrane in a Roller Blot hybridisation oven (Techne) for 2 h at room temperature. The membrane was then washed with 3 changes of PBS-T buffer for 5 min each. An antimouse peroxidase conjugate was diluted 1:25,000 in 40 ml of PBS-T and added to the membrane in a Roller Blot hybridisation oven (Techne) for 1 h at room temperature. The membrane was then washed with 3 changes of PBS-T buffer for 5 min each. Detection of proteins was using chemiluminescent substrates for horseradish peroxidase (Amersham ECL reagent) and autoradiography (FIG. 4). Signals were quantified by densitometry.

Stripping of Membrane

Antibodies were removed by incubating the membrane in stripping buffer (PBS; 2% SDS w/v; 100 mM beta mercaptoethanol) for 30 min at room temperature. The membrane was then washed for 30 min in PBS-T and then blocked with Superblock.

Detection of Biotinylated Proteins

Figure 5C:
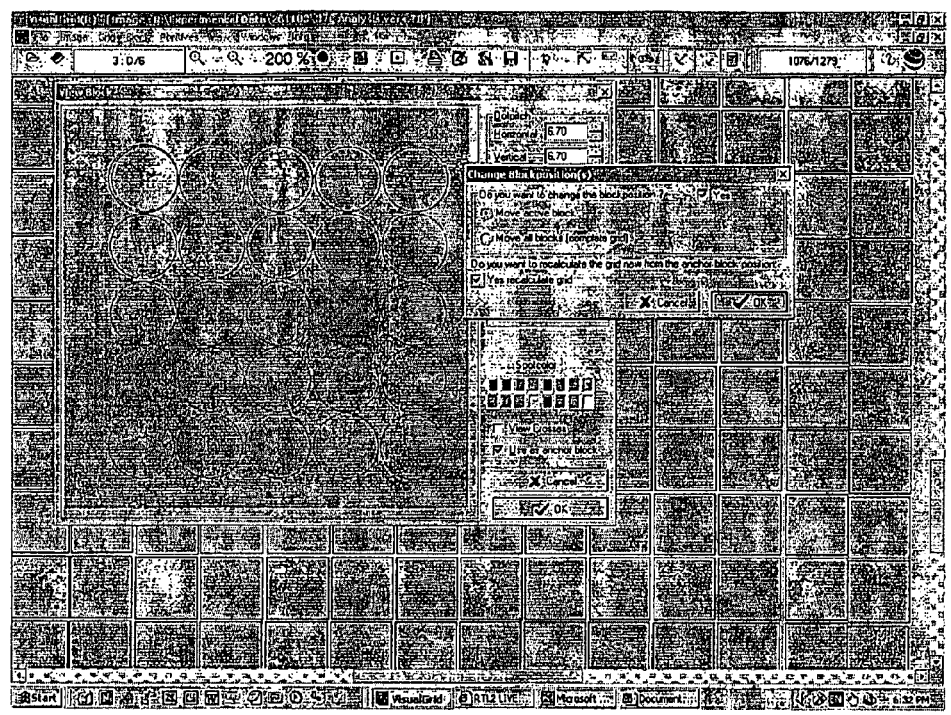
FIG. 5: Expression analysis showing identification of biotinylated proteins indicating solubility. One field out of six is shown in the FIGS. 5a and 5b and comprises a 5×5 array (24 plates per field). Proteins are identified through binding of a streptavidin-horseradish conjugate. Results were obtained from replicate arrays uninduced prior to cell lysis (FIG. 5a) and induced with IPTG (FIG. 5b). Evidence of IPTG-induced protein expression can be seen on the second membrane. Slides are analysed quantitatively (5c) using image analysis software (VisualGrid; GPC Biotech).

Excess blocking reagent was removed by washing in PBS-T for 5 min. Streptavidin-horseradish peroxidase was diluted 1:25,000 in 40 ml of PBS-T and added to the membrane in a Roller Blot hybridisation oven (Techne) for 1 h at room temperature. The membrane was then washed with 3 changes of PBS-T buffer for 5 min each. Detection of proteins was using chemiluminescent substrates for horseradish peroxidase (Amersham ECL reagent) and autoradiography. FIG. 5 shows the results of the Streptavidin screen for soluble protein. Results obtained from duplicate arrays uninduced and induced with IPTG prior to cell lysis (FIGS. 5a and 5b respectively) are shown. Evidence of IPTG-induced protein expression can be seen on the second membrane (5b).

Figure 16:
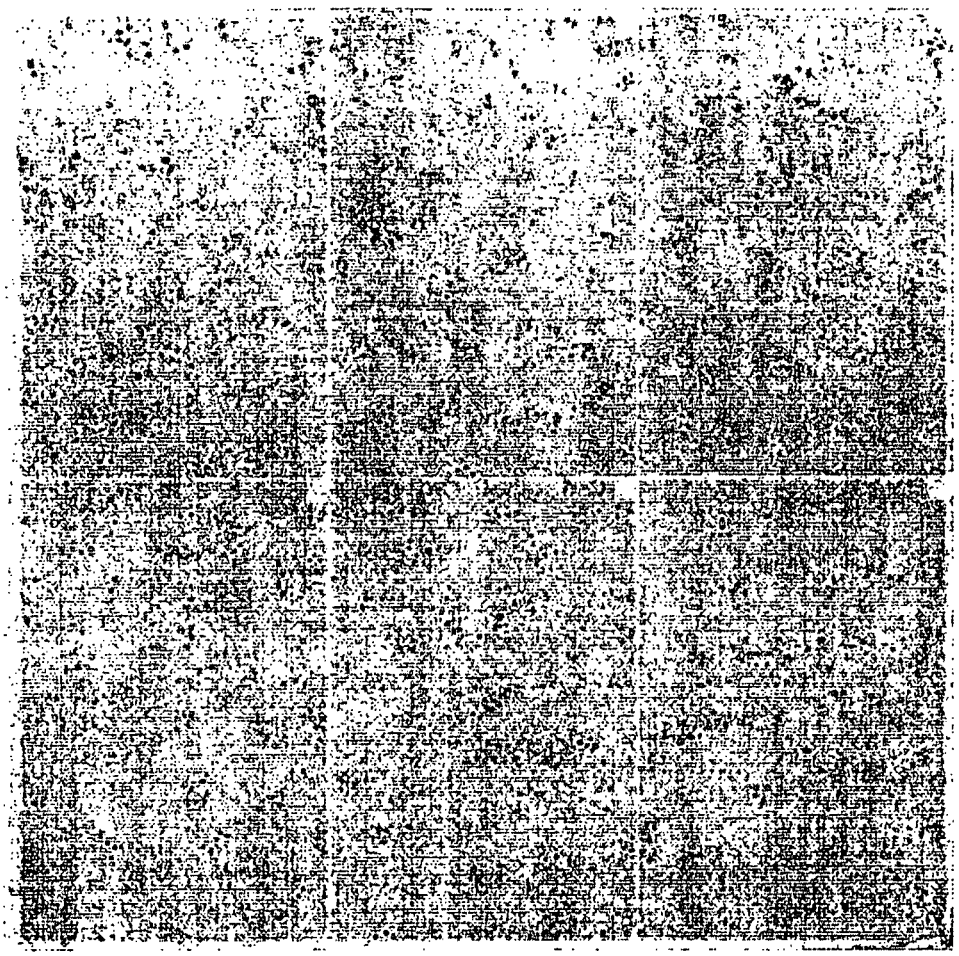
FIG. 16: Solubility screen of proteins expressed by the random truncation library clones of the gene in plasmid pHAR1111. Here the array was probed with Alexa488 fluorophor conjugated streptavidin and the image captured via a Typhoon fluorescence scanner (Amersham). Clones expressing soluble proteins are visible in a duplicate pattern for each.

An alternative, more quantitative method for detection uses fluorescence and is presented in addition to the chemiluminescent method above: The same library of the candidate gene was prepared as an array as above and then biotinylated proteins detected using a fluorescent Alexa4 μg-streptavidin conjugate (Molecular Probes). The membrane was then scanned using a Typhoon imager (Amersham) and the image analysed using software VisualGrid (GPC Biotech) (FIG. 16).

Data Analysis

Signals from the array were quantified by densitometry and clones were ranked for expression level using image analysis software (5c) and prioritised for further study. Of the 27000 clones analysed, about 300 were selected for further analysis since the data indicated expression of soluble protein.

Analysis of Unselected and Selected Clones

Figure 14:
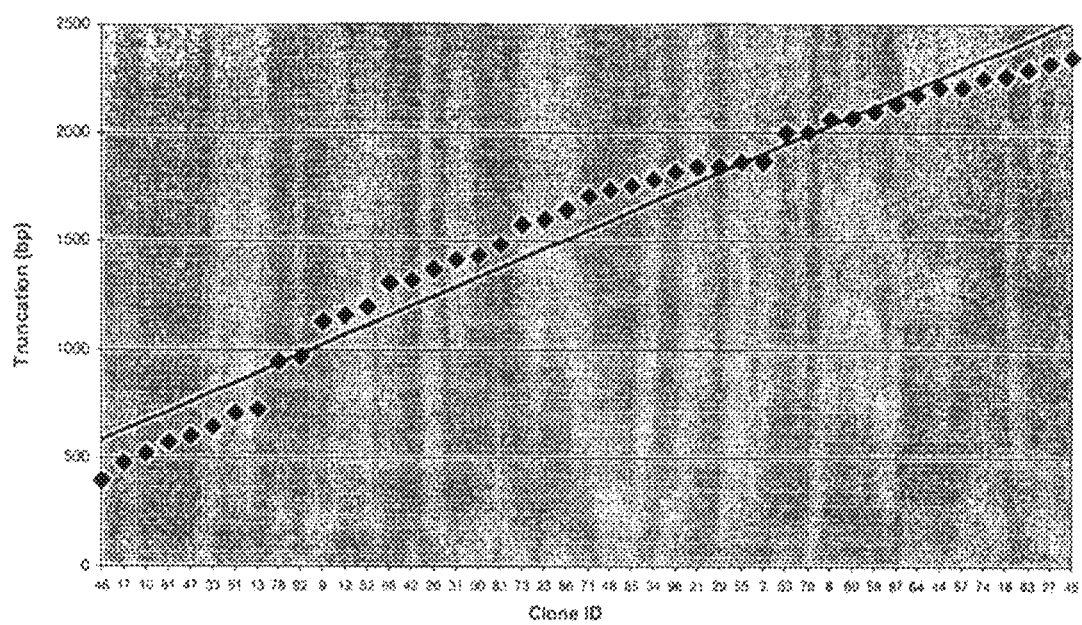
FIG. 14: Size distribution of the gene inserts from plasmid pHAR1111 (see FIG. 1) as revealed by plasmid digest. It is apparent that the exonuclease truncation protocol as performed here generates a linear and relatively unbiased distribution of gene fragment sizes permitting screening of random truncations of the target gene of all sizes.
Figure 15:
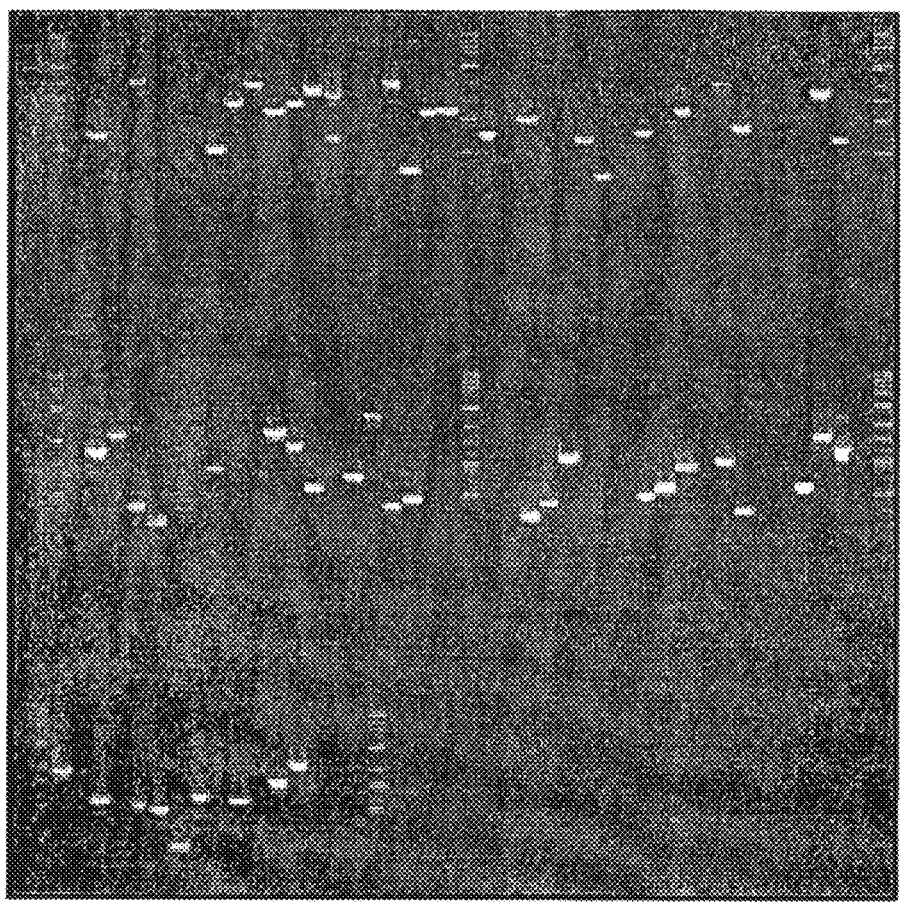
FIG. 15: Results of PCR analysis of the randomly truncated gene from plasmid pHAR1111 showing size distribution of a sample of clones in the library before solubility screening.
Figure 17:
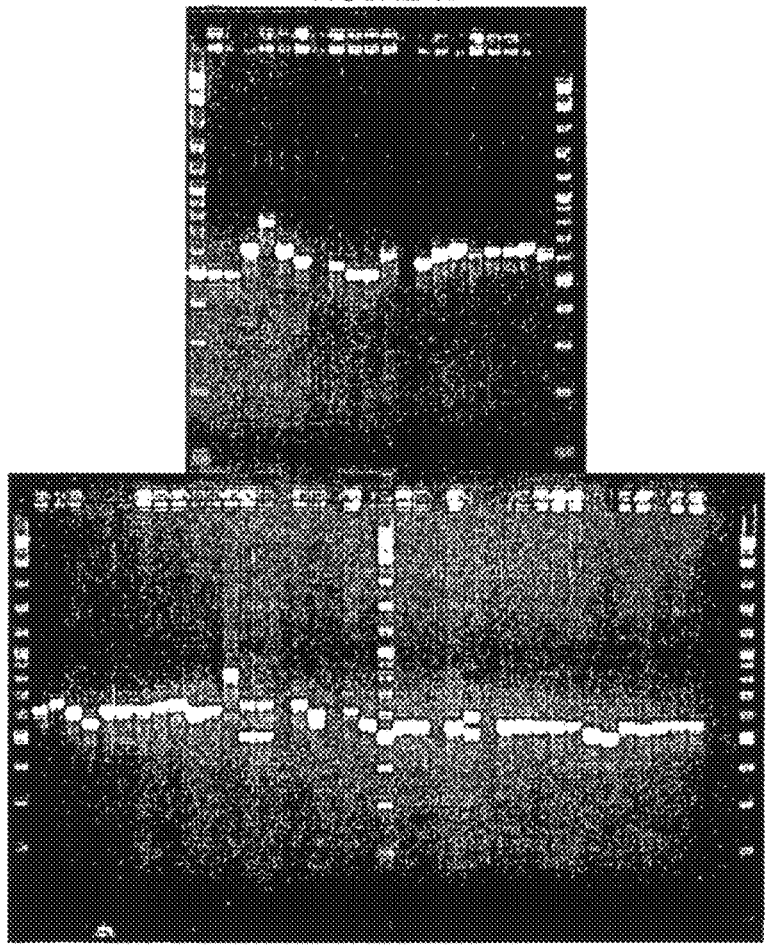
FIG. 17: Results of PCR analysis of the randomly truncated gene from plasmid pHAR1111 showing the non-random size distribution of truncations expressing soluble protein.

Clones from the library of the previously unexpressed candidate gene of pHAR1111 which were identified as expressing soluble, stable protein from the array data were robotically extracted from the frozen bank using the rearraying functionality of the picker-gridder robot. Insert size was screened using PCR screen of 96 clones with flanking primers and agarose gel electrophoresis. The same analysis was also performed on a random selection of clones from the library for comparison in order to determine the quality of the library. The PCR results to the randomly picked clones are displayed in FIG. 15. A graph showing the analysis of this PCR data is presented in FIG. 14 and it can be observed that there is a linear and relatively unbiased distribution of truncation lengths. The PCR products were digested using NdeI to confirm the start codon. The PCR analysis of clones identified as best soluble expressers from the fluorescence analysis is shown in FIG. 17 and it is clear that the distribution of truncation sizes is no longer random, but clusters around a similar size.

Protein expression of the first 96 best expressers (same library but from the earlier chemiluminescent detection method) was verified by western blot and it was confirmed that the proteins were soluble by filtration-based fractionation of expression lysates (FIG. 13) and matched the predicted insert size.

Figure 11:
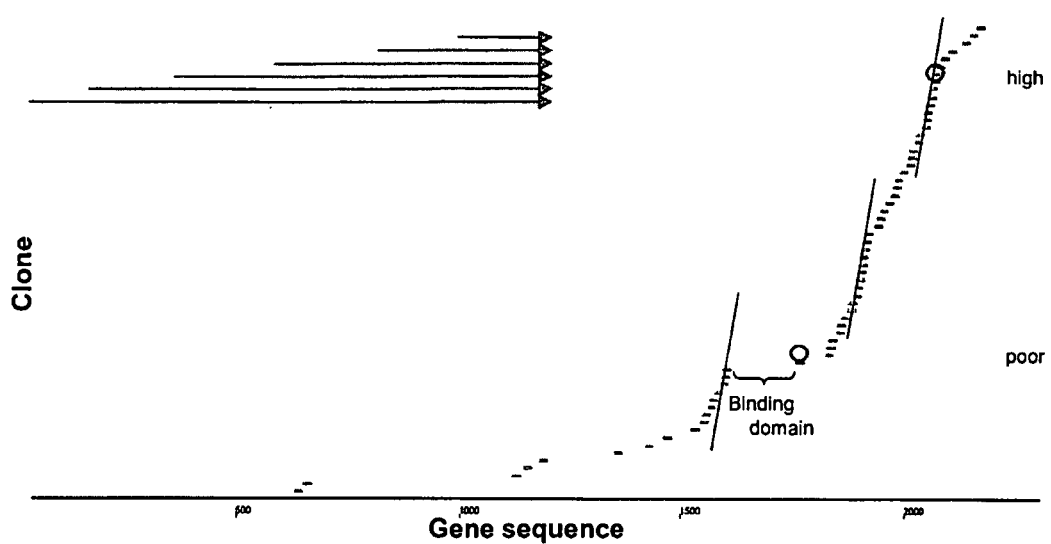
FIG. 11: Soluble expression map of the gene encoding a previously unexpressed protein correlating solubility with genetic truncation point. The positions of new start codons generated during construction of a N-terminal truncation library are aligned against the full-length gene sequence. Of the 2400 positions, 61 are indicative of soluble protein expression. The figure demonstrates a binary output (expression above a threshold limit vs non-expression) however some clones express much better than others (examples of low and high expressing clones are indicated).

Solubly expressing clones of the previously unexpressed candidate gene were then sequenced using vector specific primers with sequence reading across the truncated gene to identify both the exact identity of the truncation boundaries and replicates (where the same clone was recovered multiple times). The latter occurs because, on average, each position of the protein was tested 7-fold. Using these data, experimentally determined clones were aligned against the full-length gene resulting in a soluble expression map (FIG. 11). Such a map is unique and has never been produced previously for a protein. It illustrates the positions in a protein where it can be truncated and produce soluble protein. Multiple clones are identified and these can be further prioritised by a) selecting those that give a high signal on the membrane array and western blots when probed with streptavidin i.e. express well b) selecting those that are smallest when consecutive amino acids are identified as truncation points. The latter is an advantage when clones are to be used for X-ray crystallography, as compact proteins with ordered termini usually crystallise more efficiently than proteins with appended, disordered peptide. This resolution of information is only possible due to the oversampling of the experiment made possible by the high throughput nature of the screening method.

As can be seen, there is a degree of order evident from portraying the degree of solubility of the various clones ranked according to the sequence of the encoding gene. Similar levels of solubility are evident in constructs with consecutive truncations (see straight lines drawn through marker points), and these are believed to correspond to regions of consecutive residues in solvent-exposed linkers. In contrast, gaps of poor solubility are evident from truncation boundaries that fall within structured regions in the protein (see region marked as "binding domain" in FIG. 11).

It is hypothesised herein that this type of analysis allows an exhaustive analysis of the solubility of truncated variants of a protein to divulge information on protein structure, such as domain boundaries, and the degree of solvent exposure of residues in the primary structure of the protein. This forms a further aspect of the present invention.

Protein Expression Colony vs Liquid

Figure 13:
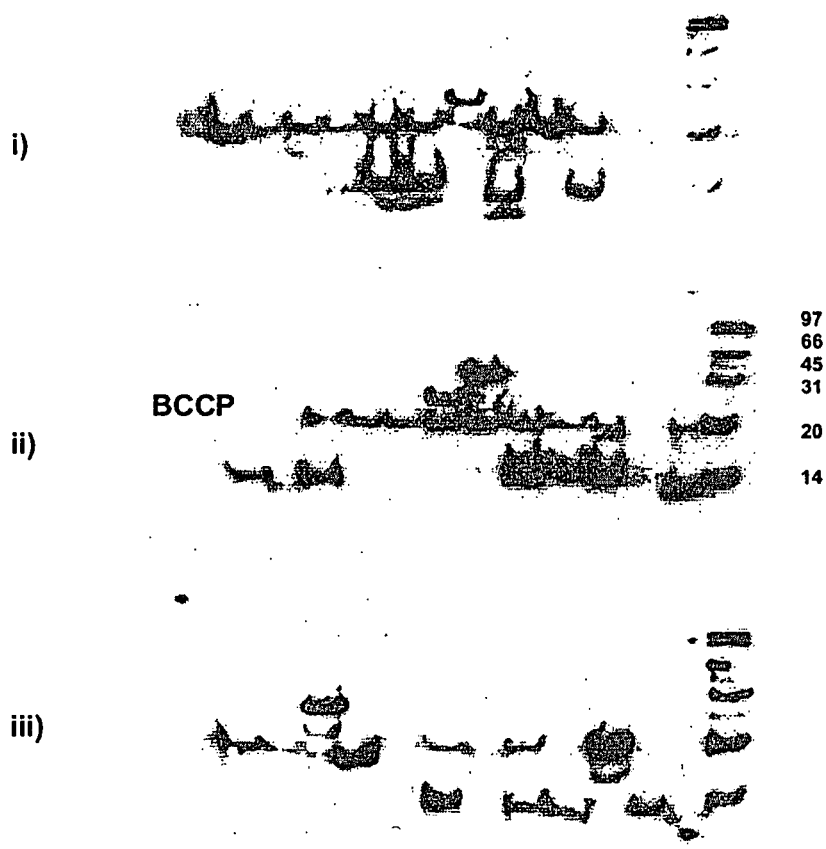
FIG. 13: Protein expression as identified using Western blot analysis. 96 positive clones from the truncation library of the gene in plasmid pHAR1111 were grown in LB. Cells were lysed, fractionated and soluble fractions were analysed by Western blot with Str-HRP. Some representative clones are shown. Recombinant proteins from Western analyses cluster according to 3 size ranges (approx 10, 20, 30 kDa) as apparent from the soluble expression map in FIG. 11. The endogenous host protein BCCP is also indicated.

FIG. 13 shows Western blot analysis of positive clones grown up in LB culture medium, lysed and fractionated into soluble fractions. A wide range of expression level is evident, although 3 clusters of 10 kDa, 20 kDa and 30 kDa can be distinguished that are also apparent in the soluble expression map (FIG. 11). The full-length protein is 86 kDa and absence of larger constructs is thought to be a consequence of the architecture of this particular target. This result also demonstrates that protein expression as measured in colonies correlates well with that of the more standard liquid culture format.

Scale-up of Protein Expression and Further Characterisation

Figure 18:
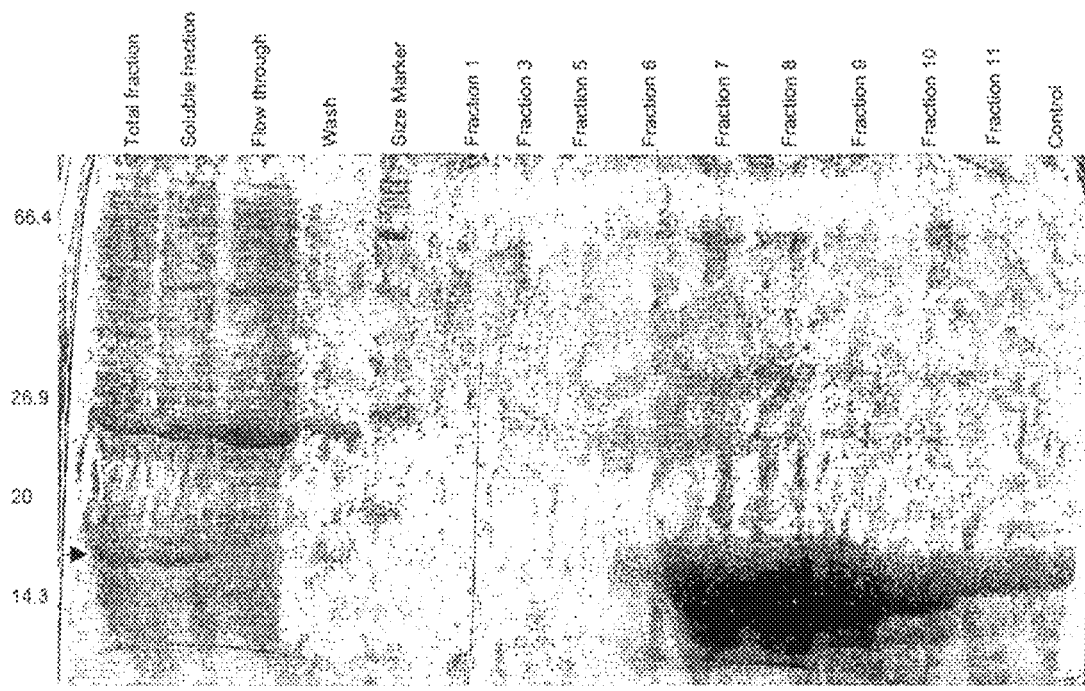
FIG. 18: Purification profile of a soluble protein fragment identified using the solubility screen. The gene fragment was first subcloned into an E. coli expression vector to add a N-terminal hexahistidine tag to facilitate purification (FIG. 19).
Figure 19:
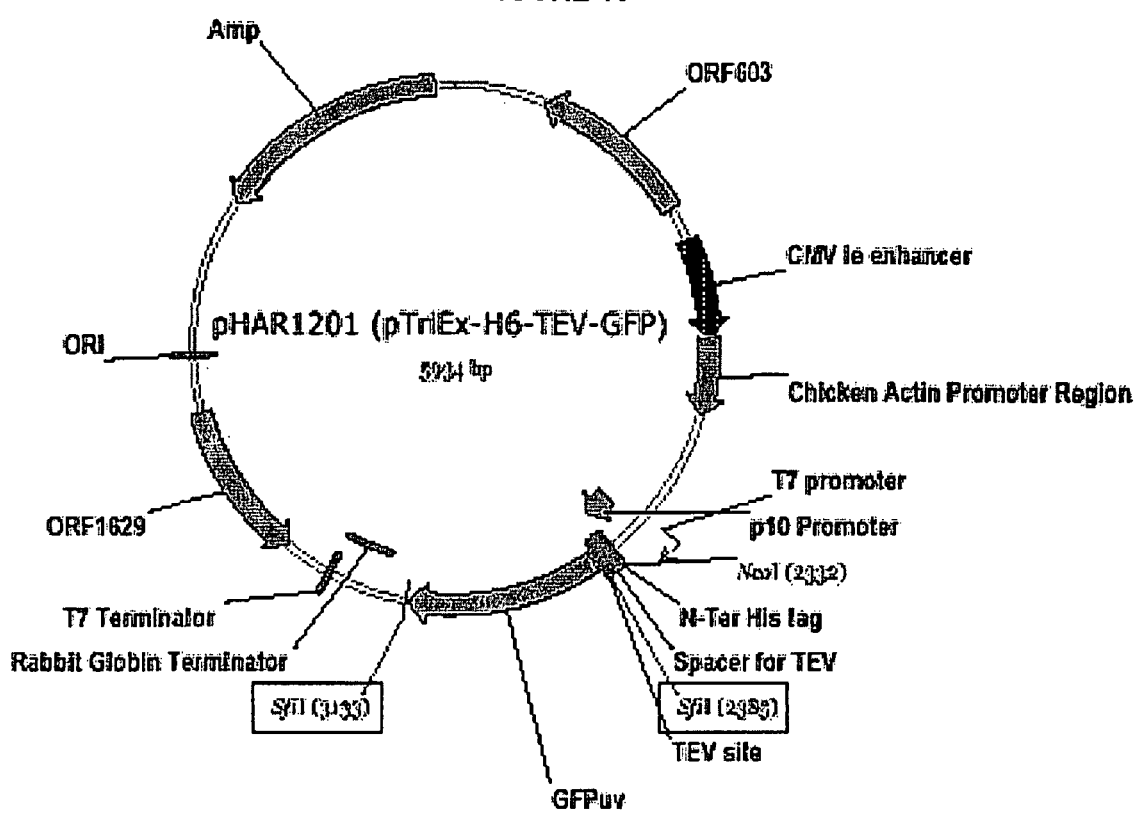
FIG. 19: A derivative of the pTriEX vector (Novagen) that was used to subclone gene fragments for scale-up of protein expression. A TEV protease cleavable hexahistidine tag is added to the N-terminal end of the construct to permit affinity purification.
Figure 21:
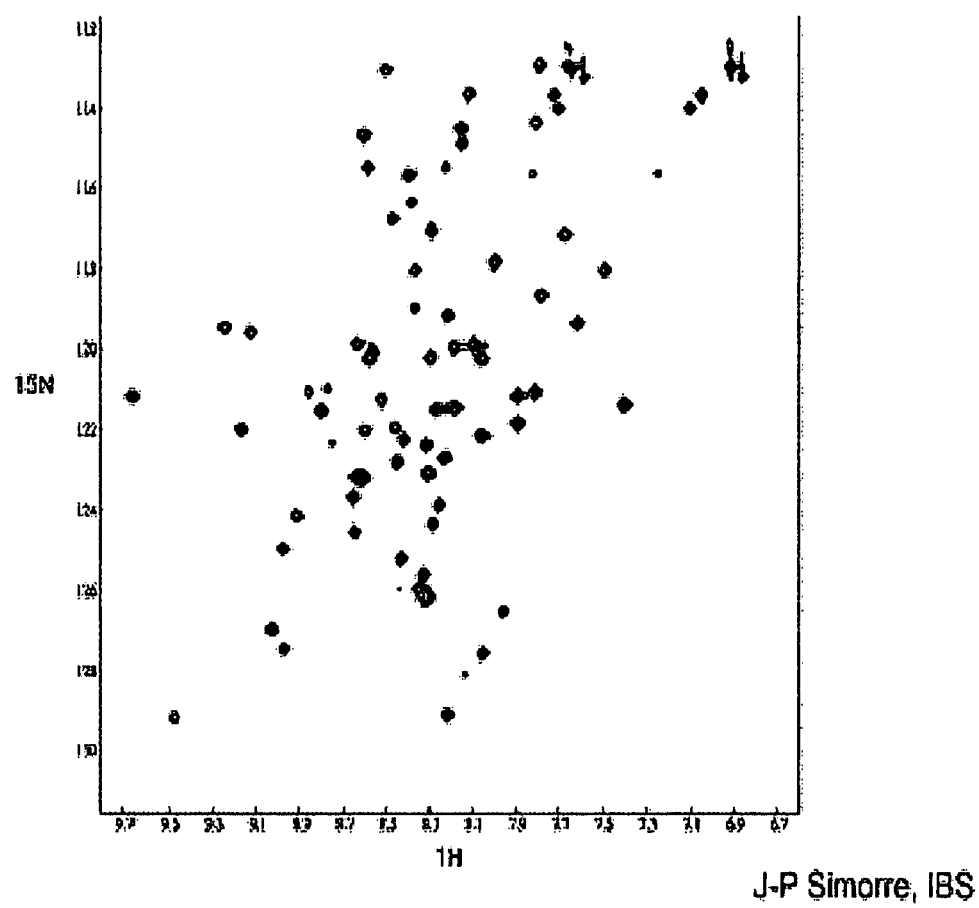
FIG. 21: Results of an HQSC NMR spectrum analysis of $^{15}$N labelled protein which confirm that the purified domain identified from the screening of the random library is well-folded in addition to being highly soluble.

One of the genetic constructs identified above as expressing purified protein was subcloned into a pTriEX derivative vector (Novagen) (FIG. 19) for improving protein expression through use of a stronger T7-based promoter and for aiding purification via addition of a N-terminal hexahistidine tag that can be removed by cleavage with TEV protease. Expression of this particular construct was good at approximately 40 mg per liter and lead to easily purifiable material. This is demonstrated by SDS-PAGE analysis of the purification fractions (FIG. 18). The purified protein shown here was further characterised for foldedness using NMR and the HQSC spectrum of $N^{15}$ labelled material is shown in FIG. 21. This particular protein has proceeded to a full structure solution by NMR showing that it does comprise a folded, soluble and globular domain from a protein that has never been overexpressed successfully before, thus demonstrating the utility of the current invention. The clone has also been used for crystallisation studies.

Figure 20:
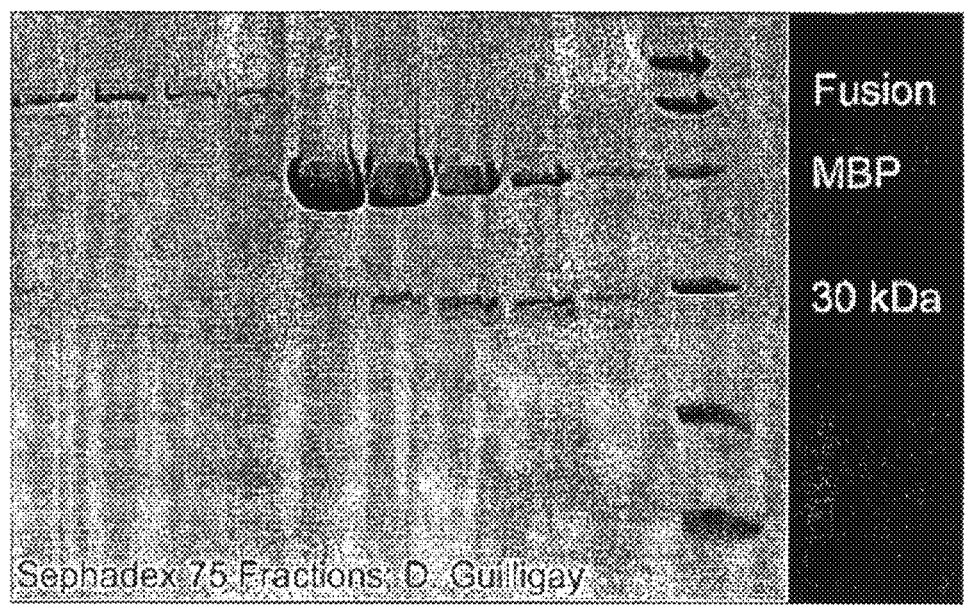
FIG. 20: A multidomain 30 kDa fragment of the protein expressed from pHAR1111 is obtained after fusion of the truncated gene to maltose binding protein to aid expression and purification.

Additionally, a second larger 30 kDa protein of this target has been produced using the information from the soluble expression map to guide the selection of clones (FIG. 11) and comprises the smaller domain from above plus another 20 kDa of material. It is expected that this comprises at least two domains. This protein was effectively expressed from both the pTriEX system (FIG. 19) and also a pMAL vector (New England Biolabs) that produces an easily purifiable maltose binding protein fusion which is shown here in FIG. 20.

Analysis of NF-Kappa B: an Additional Example of the Invention Employing a Protein of Known Structure for Validation Purposes The first example shown above in detail was of a previously intractable protein since it was not possible to express the protein prior to this work. However it was also considered necessary to perform the same process on a protein of known structure in order to validate the method further. The protein NF-kappa B was chosen since it has a well-defined domain structure. Two libraries were constructed using pHAR1112 for N-terminal truncation (FIG. 2) and pMAS106 (FIG. 3) for C-terminal truncation. The libraries were constructed as for the example above with the exception that pMAS106 was digested with FseI and XbaI prior to the exonuclease truncation step.

Figure 6:
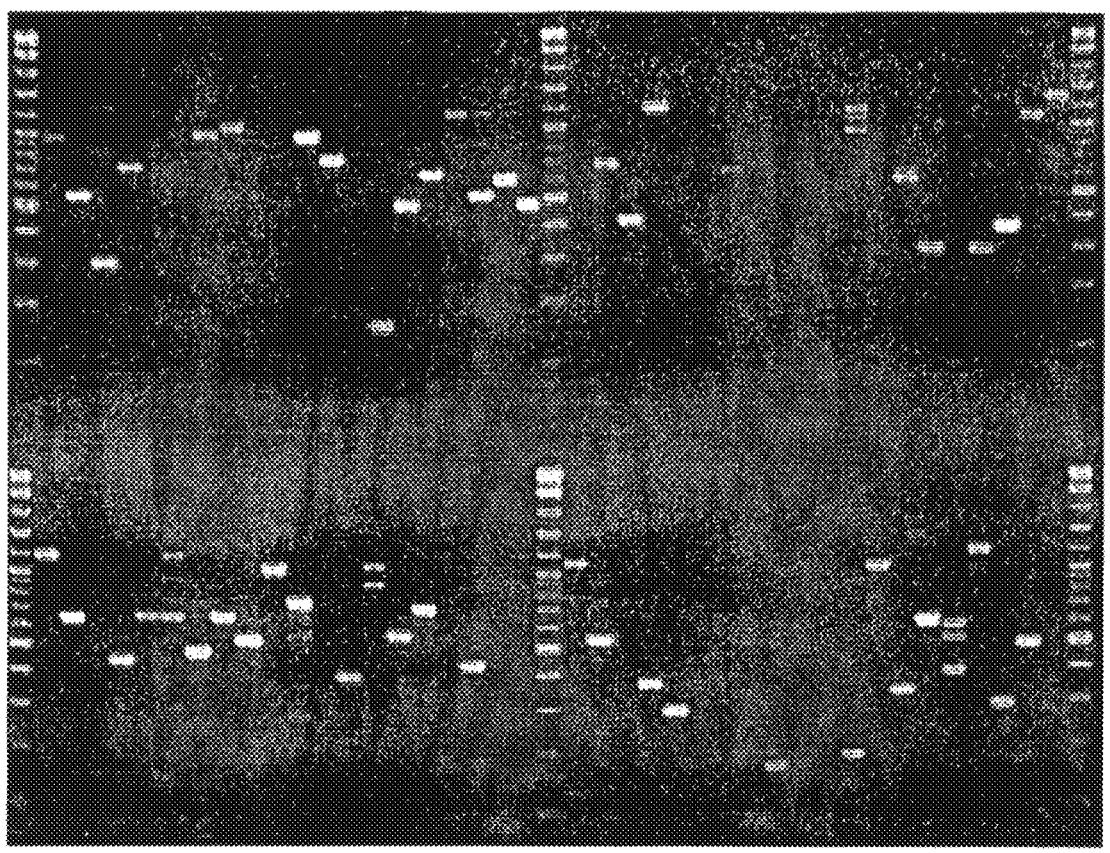
FIG. 6: Sizing of truncated NF-κB truncated inserts by PCR reveals a random size distribution.
Figure 7:
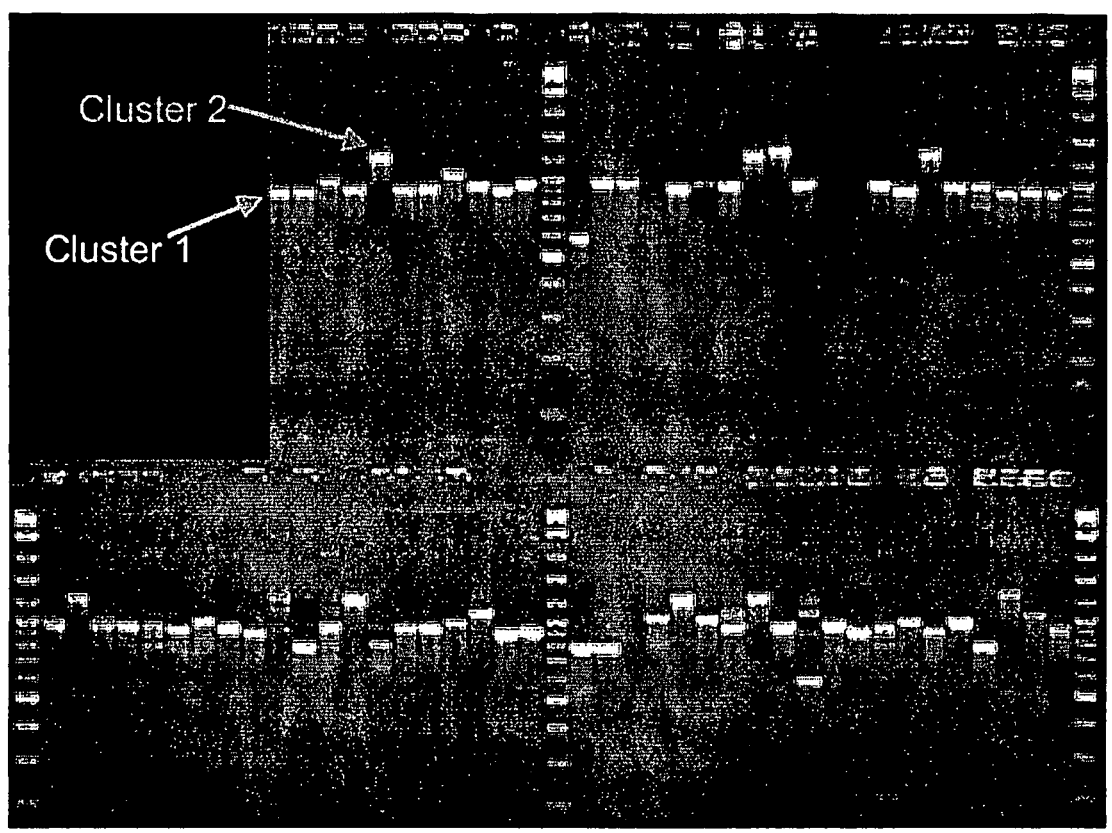
FIG. 7: DNA fragments sized by PCR of the expression plasmids using flanking oligonucleotide primers. Clones expressing soluble truncated NF kappa B protein can be organised into 2 clusters indicative of one and two domain constructs (approximately 25 kDa and 40 kDa predicted size).
Figure 8:
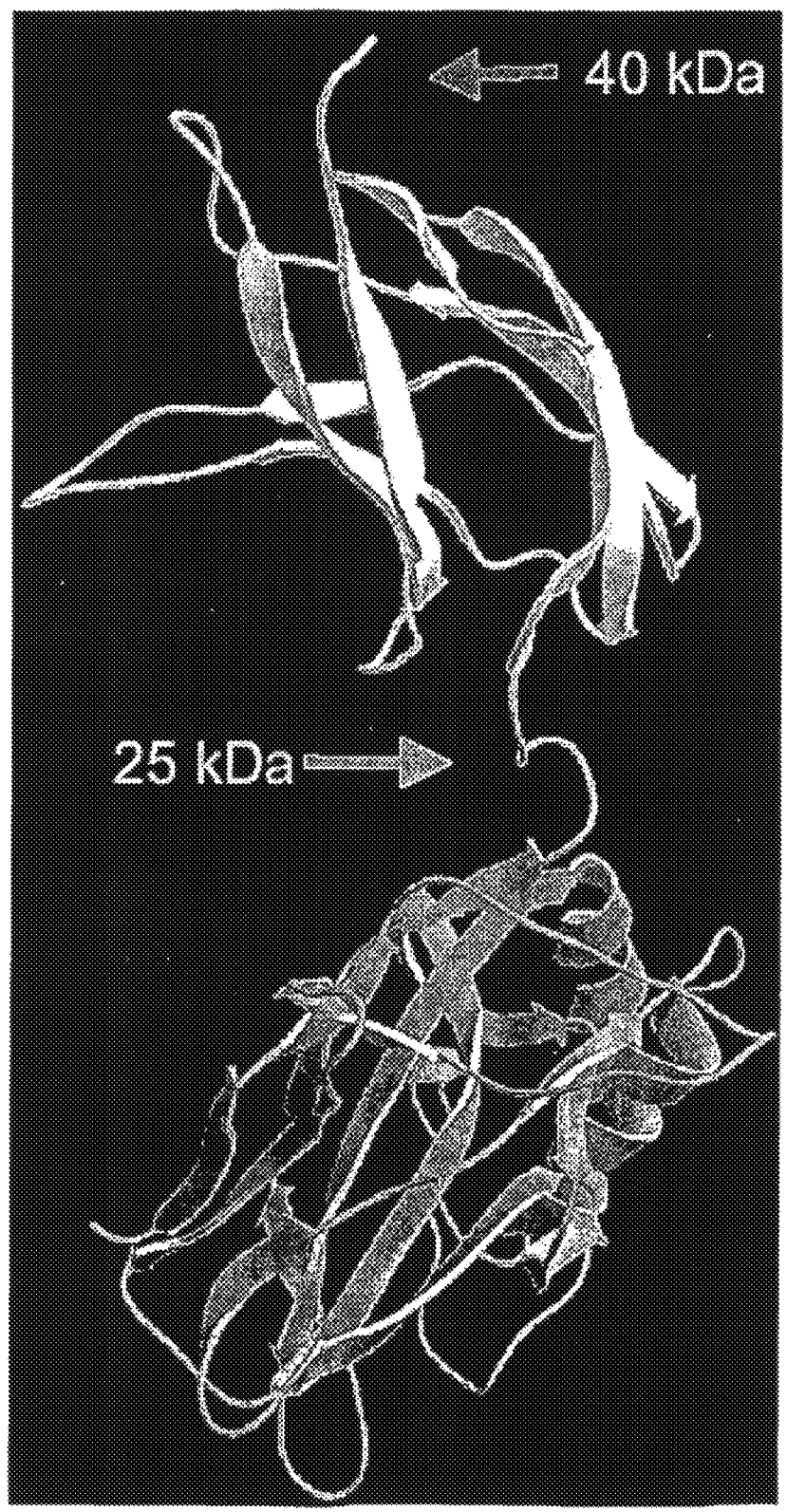
FIG. 8: Structure of the NF-κB protein indicating the size of the one and two domain protein fragments when truncated from the C-terminus.
Figure 9:
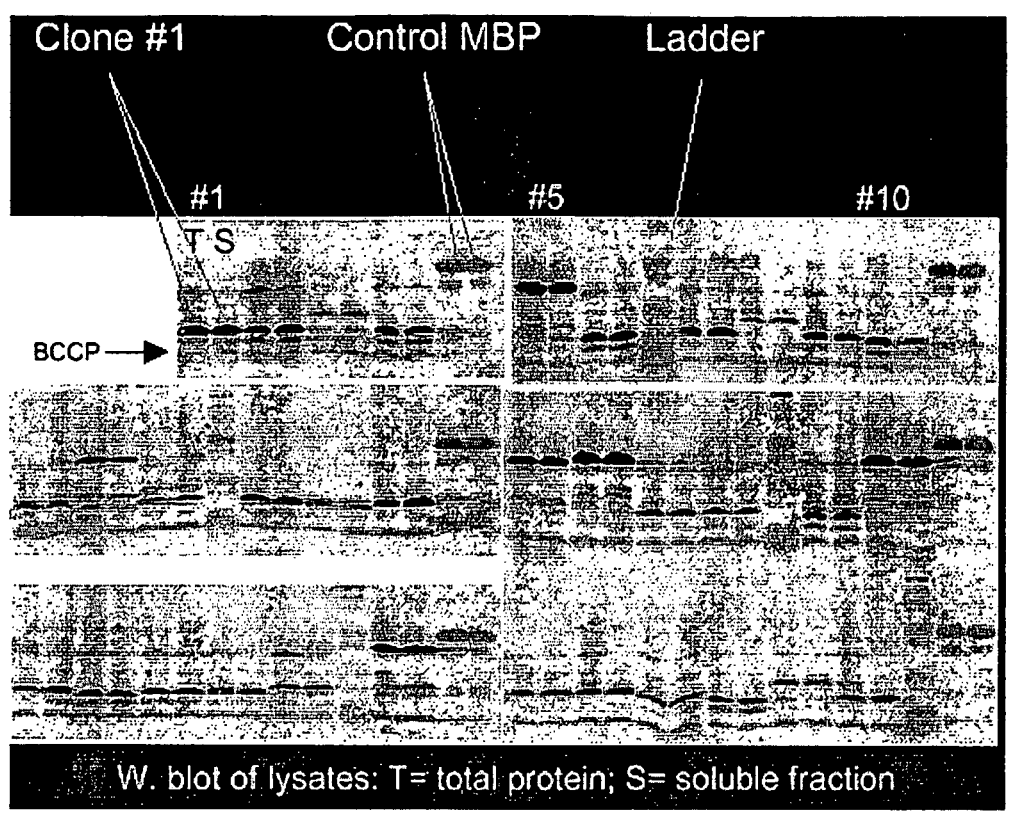
FIG. 9: Protein expression screen of the 48 best expressing NF-κB clones by Western blot. There is no significant difference between the total (T) and soluble (S) fractions for each clone indicating the clones identified by the screen are soluble. Faint expression of the E. coli endogenous BCCP protein is also visible since it is the only other biotinylated protein in the cell.
Figure 10:
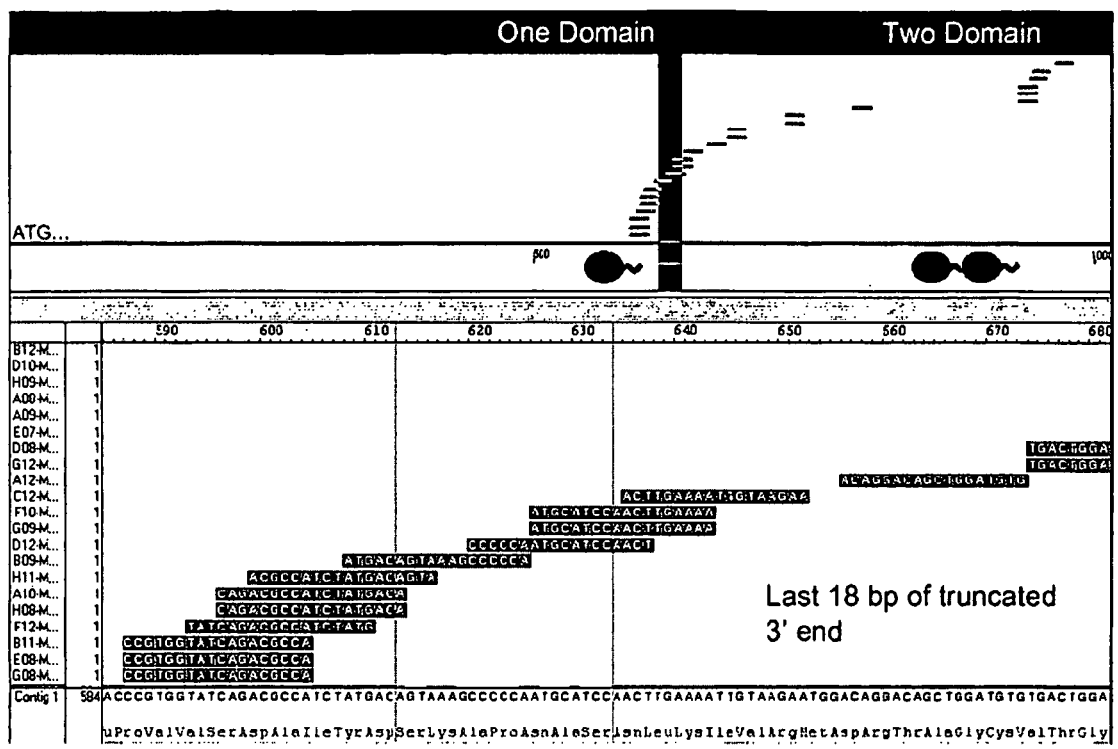
FIG. 10: Definition of exact truncation termini by alignment of the last 18 base pairs of DNA sequencing data at the truncated 3' end with the full-length gene sequence (SEQ ID NO: 11). The truncated sequences, starting with the uppermost 18 bp sequence, correspond to SEQ ID NOs 12-20, respectively.

The quality of the C-terminal truncation library from pMAS106 was measured by PCR of the gene fragment inserts with flanking primers as above and the results are shown in FIG. 6. The array of colonies was analysed using the fluorescent method with Alexa488-streptavidin conjugate as described above. The positive clones were isolated from the main library using the cherry picking function of the picker-gridder robot and the most intense 96 clones analysed by PCR. The results (FIG. 7) reveal 2 size clusters of DNA that are predicted to encode proteins of approximately 25 kDa and 40 kDa. These predicted sizes correlate well with the domain structure of NF-kappa B (FIG. 8). The first 48 clones were expressed in LB liquid cultures and total and soluble lysates were prepared. Analysis by western blot (FIG. 9) indicates that all proteins are totally soluble and that the protein sizes observed closely match the predicted sizes from the PCR screen (FIG. 7). All soluble clones were sequenced and the new C-termini generated by truncation were aligned against the protein sequence resulting in a soluble expression map for NF-kappa B (FIG. 10). The domain structure of the protein is clearly revealed and the edges of the domains mapped at single amino acid resolution by selecting the smallest, most compact form of each domain (FIG. 12). Both the two domain 40 kDa and one domain 25 kDa constructs have been previously characterised in the scientific literature as being functional for DNA binding. Thus the domains identified by the screening for soluble expression of the randomly truncated NF-kappa B gene are both soluble and functional.

The invention claimed is:

1. A method of screening for a soluble variant within a plurality of variants of an insoluble protein comprising
generating a plurality of variants of the insoluble protein wherein each variant is fused to a peptide substrate of 50 amino acids in length or smaller,
contacting the variants with an enzyme capable of modifying the peptide substrate, and
detecting enzymatic modification of the peptide substrate,
wherein:
each variant either comprises up to 10 substitutions, deletions and/or additions to the amino acid sequence of the insoluble protein or is a truncated version of the insoluble protein;
the peptide substrate is linear, possesses no tertiary structure and does not significantly perturb the solubility of each of the variants; and
enzymatic modification of the peptide substrate indicates that the variant fused to the peptide substrate is a soluble variant of the insoluble protein.

2. The method according to claim 1, wherein the plurality of variants are generated by expression from vectors contained within a library of host cells.

3. The method according to claim 2, wherein each host cell in the library expresses a substrate-modifying enzyme that is capable of modifying the peptide substrate.

4. The method according to claim 2, wherein said host cells are $E. coli$ cells.

5. The method according to claim 4, wherein said $E. coli$ cells express biotin protein ligase.

6. The method according to claim 1, wherein said plurality of variants comprises a truncation library of the insoluble protein.

7. The method according to claim 6, wherein said library is generated by exonuclease digestion of nucleic acids encoding the insoluble protein.

8. The method according to claim 6, further comprising the step of correlating information regarding the solubility of the variants with the protein sequence of the insoluble protein.

9. A method for obtaining information relating to protein structure, the method comprising performing the method according to claim 6, further comprising the step of correlating information regarding the solubility of the variants with the protein sequence of the insoluble protein.

10. A method of obtaining a soluble variant of an insoluble protein, comprising
providing a plurality of variants of the insoluble protein wherein each variant is fused to a peptide substrate of 50 amino acids in length or smaller,
contacting the variants with an enzyme capable of modifying the peptide substrate, and
detecting enzymatic modification of the peptide substrate,
wherein:
each variant either comprises up to 10 substitutions, deletions and/or additions to the amino acid sequence of the insoluble protein or is a truncated version of the insoluble protein;
the peptide substrate is linear, possesses no tertiary structure and does not significantly perturb the solubility of each of the variants; and
enzymatic modification of the peptide substrate indicates that the variant fused to the peptide substrate is a soluble variant of the insoluble protein.

11. The method according to claim 10, wherein the peptide substrate does not significantly perturb the physical characteristics of the variant to which it is fused.

12. The method according to claim 10, wherein the peptide substrate is between 5 and 20 amino acids in length.

13. The method according to claim 10, wherein the peptide substrate is a substrate for biotin protein ligase.

14. The method according to claim 13, wherein the peptide substrate is GLNDIFEAQKIEWHE (SEQ ID NO: 1).

15. The method according to claim 10, wherein the peptide substrate is fused to each variant by a peptide bond.

16. The method according to claim 10, wherein the peptide substrate is fused at the carboxy terminus of the variant.

17. The method according to claim 10, wherein the peptide substrate is fused at the amino terminus of the variant.

18. The method according to claim 10, wherein said plurality of variants are screened for solubility using colony arrays.

19. The method according to claim 18, wherein the variants expressed by colonies in the arrays are screened for solubility by detection of modified peptide substrate using an antibody or detection reagent selective for the modified peptide substrate.

* * * * *

SEQUENCE LISTING

<160> NUMBER OF SEQ ID NOS: 20

<210> SEQ ID NO 1
<211> LENGTH: 15
<212> TYPE: PRT

<213> ORGANISM: E.coli

<400> SEQUENCE: 1

Gly Leu Asn Asp Ile Phe Glu Ala Gln Lys Ile Glu Trp His Glu
1               5                   10                  15

<210> SEQ ID NO 2
<211> LENGTH: 10
<212> TYPE: PRT
<213> ORGANISM: Artificial Sequence
<220> FEATURE:
<223> OTHER INFORMATION: Kinase peptide substrate

<400> SEQUENCE: 2

Arg Arg Arg Asp Asp Asp Ser Asp Asp Asp
1               5                   10

<210> SEQ ID NO 3
<211> LENGTH: 66
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: 40...66
<223> OTHER INFORMATION: n is a, c, g or t and indicates a complimentary
      base to the candidate gene sequence

<400> SEQUENCE: 3
gatcctagca tatgaaatgc atggatccgc ggccgctgan nnnnnnnnn nnnnnnnnnn    60 nnnnnn                                                              66

<210> SEQ ID NO 4
<211> LENGTH: 24
<212> TYPE: DNA
<213> ORGANISM: Artificial Sequence
<220> FEATURE:
<223> OTHER INFORMATION: PCR primer

<400> SEQUENCE: 4
gatcctagca tatgaaatgc atgg                                          24

<210> SEQ ID NO 5
<211> LENGTH: 43
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: 17...43
<223> OTHER INFORMATION: n is a, c, g or t and indicates a complimentary
      base to the candidate gene sequence

<400> SEQUENCE: 5
gatcctaggg ccggccnnnn nnnnnnnnnn nnnnnnnnnn nnn                     43

<210> SEQ ID NO 6
<211> LENGTH: 21
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: 17...21
<223> OTHER INFORMATION: n is a, c, g or t and indicates a complimentary
      base to the candidate gene sequence

```
<400> SEQUENCE: 6
gatcctaggg ccggccnnnn n                                              21

<210> SEQ ID NO 7
<211> LENGTH: 67
<212> TYPE: DNA
<213> ORGANISM: Artificial Sequence
<220> FEATURE:
<223> OTHER INFORMATION: PCR primer

<400> SEQUENCE: 7
agcttgcttg gtggcggtct gaacgacatc ttcgaggctc agaaaatcga atggcacgaa    60
taatgag                                                              67

<210> SEQ ID NO 8
<211> LENGTH: 67
<212> TYPE: DNA
<213> ORGANISM: Artificial Sequence
<220> FEATURE:
<223> OTHER INFORMATION: PCR primer

<400> SEQUENCE: 8
agctctcatt attcgtgcca ttcgattttc tgagcctcga agatgtcgtt cagaccgcca    60
ccaagca                                                              67

<210> SEQ ID NO 9
<211> LENGTH: 48
<212> TYPE: DNA
<213> ORGANISM: Artificial Sequence
<220> FEATURE:
<223> OTHER INFORMATION: PCR primer

<400> SEQUENCE: 9
ggatccgcgg ccgctgagca gatggcccat accttcaaat attagagc                 48

<210> SEQ ID NO 10
<211> LENGTH: 43
<212> TYPE: DNA
<213> ORGANISM: Artificial Sequence
<220> FEATURE:
<223> OTHER INFORMATION: PCR primer

<400> SEQUENCE: 10
gggatccggc cggcccttc tgacgtttcc tctgcacttc ttc                       43

<210> SEQ ID NO 11
<211> LENGTH: 97
<212> TYPE: DNA
<213> ORGANISM: Artificial Sequence
<220> FEATURE:
<223> OTHER INFORMATION: Synthetic Construct; NF kappa-B fragment
<220> FEATURE:
<221> NAME/KEY: CDS
<222> LOCATION: (2)..(97)

<400> SEQUENCE: 11 a ccc gtg gta tca gac gcc atc tat gac agt aaa gcc ccc aat gca tcc   49
  Pro Val Val Ser Asp Ala Ile Tyr Asp Ser Lys Ala Pro Asn Ala Ser
  1               5                  10                  15 aac ttg aaa att gta aga atg gac agg aca gct gga tgt gtg act gga    97
Asn Leu Lys Ile Val Arg Met Asp Arg Thr Ala Gly Cys Val Thr Gly
            20                  25                  30

<210> SEQ ID NO 12
```

```
<211> LENGTH: 18
<212> TYPE: DNA
<213> ORGANISM: Artificial Sequence
<220> FEATURE:
<223> OTHER INFORMATION: Synthetic Construct; NF kappa-B fragment

<400> SEQUENCE: 12
acaggacagc tggatgtg                                                18

<210> SEQ ID NO 13
<211> LENGTH: 18
<212> TYPE: DNA
<213> ORGANISM: Artificial Sequence
<220> FEATURE:
<223> OTHER INFORMATION: Synthetic Construct; NF kappa-B fragment

<400> SEQUENCE: 13
acttgaaaat tgtaagaa                                                18

<210> SEQ ID NO 14
<211> LENGTH: 18
<212> TYPE: DNA
<213> ORGANISM: Artificial Sequence
<220> FEATURE:
<223> OTHER INFORMATION: Synthetic Construct; NF kappa-B fragment

<400> SEQUENCE: 14
atgcatccaa cttgaaaa                                                18

<210> SEQ ID NO 15
<211> LENGTH: 18
<212> TYPE: DNA
<213> ORGANISM: Artificial Sequence
<220> FEATURE:
<223> OTHER INFORMATION: Synthetic Construct; NF kappa-B fragment

<400> SEQUENCE: 15
cccccaatgc atccaact                                                18

<210> SEQ ID NO 16
<211> LENGTH: 18
<212> TYPE: DNA
<213> ORGANISM: Artificial Sequence
<220> FEATURE:
<223> OTHER INFORMATION: Synthetic Construct; NF kappa-B fragment

<400> SEQUENCE: 16
atgacagtaa agccccca                                                18

<210> SEQ ID NO 17
<211> LENGTH: 18
<212> TYPE: DNA
<213> ORGANISM: Artificial Sequence
<220> FEATURE:
<223> OTHER INFORMATION: Synthetic Construct; NF kappa-B fragment

<400> SEQUENCE: 17
acgccatcta tgacagta                                                18

<210> SEQ ID NO 18
<211> LENGTH: 18
<212> TYPE: DNA
<213> ORGANISM: Artificial Sequence
<220> FEATURE:
<223> OTHER INFORMATION: Synthetic Construct; NF kappa-B fragment

<400> SEQUENCE: 18
```

```
cagacgccat ctatgaca                                                18

<210> SEQ ID NO 19
<211> LENGTH: 18
<212> TYPE: DNA
<213> ORGANISM: Artificial Sequence
<220> FEATURE:
<223> OTHER INFORMATION: Synthetic Construct; NF kappa-B fragment

<400> SEQUENCE: 19
tatcagacgc catctatg                                                18

<210> SEQ ID NO 20
<211> LENGTH: 18
<212> TYPE: DNA
<213> ORGANISM: Artificial Sequence
<220> FEATURE:
<223> OTHER INFORMATION: Synthetic Construct; NF kappa-B fragment

<400> SEQUENCE: 20
ccgtggtatc agacgcca                                                18
```